United States Patent
Qiang et al.

(10) Patent No.: US 10,768,318 B2
(45) Date of Patent: Sep. 8, 2020

(54) METHOD AND APPARATUS TO DETERMINE ENERGY CORRECTION ARISING FROM MULTI-CHANNEL DETECTION IN A GAMMA DETECTOR EXHIBITING NON-LINEAR ENERGY MEASUREMENT AND/OR CROSS-TALK AMONG CHANNELS

(71) Applicant: Canon Medical Systems Corporation, Otawara-shi (JP)

(72) Inventors: Yi Qiang, Vernon Hills, IL (US); Huini Du, Fremont, CA (US); Kent C. Burr, Buffalo Grove, IL (US)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 16/163,319

(22) Filed: Oct. 17, 2018

(65) Prior Publication Data

US 2020/0124750 A1 Apr. 23, 2020

(51) Int. Cl.
*G01T 1/29* (2006.01)
*G01T 7/00* (2006.01)
(Continued)

(52) U.S. Cl.
CPC .......... *G01T 1/2985* (2013.01); *A61B 6/037* (2013.01); *G01T 1/208* (2013.01); *G01T 7/005* (2013.01); *G01T 1/1644* (2013.01)

(58) Field of Classification Search
CPC ........ G01T 1/2985; G01T 1/208; A61B 6/037
See application file for complete search history.

(56) References Cited

U.S. PATENT DOCUMENTS

| 4,588,897 A | * | 5/1986 | Inbar | G01T 1/1642 250/363.07 |
| 6,727,502 B1 | * | 4/2004 | Matthews | G01T 1/1644 250/363.02 |

(Continued)

FOREIGN PATENT DOCUMENTS

| JP | 2006-058046 A | 3/2006 |
| JP | 2011-185716 A | 9/2011 |
| WO | WO 2017/071958 A1 | 5/2017 |

*Primary Examiner* — Hugh Maupin
(74) *Attorney, Agent, or Firm* — Oblon, McClelland, Maier & Neustadt, L.L.P.

(57) ABSTRACT

A method and apparatus are provided for positron emission imaging to correct a recorded energy of a detected gamma ray, when the gamma ray is scattered during detection. When scattering occurs, the energy of a single gamma ray can be distributed across multiple detector elements—a multi-channel detection. Nonlinearities in the detection process and charge/light sharing among adjacent channels can result in the summed energies from the multiple crystals of a multi-channel detection deviating from the energy that would be measured in single-channel detection absent scattering. This deviation is corrected by applying one or more correction factors (e.g., multiplicative or additive) that shifts the summed energies of multi-channel detections to agree with a known predefined energy (e.g., 511 keV). The correction factors can be stored in a look-up-table that is segmented to accommodate variations in the multi-channel energy shift based on the level of energy sharing.

21 Claims, 12 Drawing Sheets

(51) Int. Cl.
    *A61B 6/03*     (2006.01)
    *G01T 1/208*     (2006.01)
    *G01T 1/164*     (2006.01)

(56) References Cited

U.S. PATENT DOCUMENTS

2009/0166539 A1     7/2009   Ruan et al.
2011/0210255 A1*   9/2011   Kim ................. G01T 1/2985
                                                            250/362

* cited by examiner

FIG. 7A

|   |   |   |   |
|---|---|---|---|
|   | 100 |   |   |
|   |   |   |   |

FIG. 7B

|   | 5 |   |   |
|---|---|---|---|
| 5 | 80 | 5 |   |
|   | 5 |   |   |

FIG. 8A

|  |  |  |  |
|---|---|---|---|
|  | 60 | 40 |  |
|  |  |  |  |

FIG. 8B

|  | 3 | 2 |  |
|---|---|---|---|
| 3 | 48+2 | 32+3 | 2 |
|  | 3 | 2 |  |

METHOD AND APPARATUS TO DETERMINE ENERGY CORRECTION ARISING FROM MULTI-CHANNEL DETECTION IN A GAMMA DETECTOR EXHIBITING NON-LINEAR ENERGY MEASUREMENT AND/OR CROSS-TALK AMONG CHANNELS

FIELD

This disclosure relates to correcting energy measurements in a gamma-ray detector, and, more particularly, to improving energy correction for multi-channel detection events when a pixilated gamma-ray detector exhibits non-linear energy measurement and/or cross-talk among channels.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

In positron emission tomography (PET) imaging, a tracer agent is introduced into the patient, and the physical and bio-molecular properties of the agent cause it to concentrate at specific locations in the patient's body. The tracer emits positrons, resulting in an annihilation event occurs when the positron collides with an electron that produces two gamma rays (at 511 keV) traveling at substantially 180 degrees apart.

PET imaging systems use detectors positioned around the patient to detect coincidence pairs of gamma rays. A ring of detectors can be used in order to detect gamma rays coming from each angle. Thus, a PET scanner can be substantially cylindrical to be maximize the capture of the isotropic radiation. A PET scanner can be composed of several thousand individual crystals (e.g., Lutetium Orthosilicate (LYSO) or other scintillating crystal) which are arranged in two-dimensional scintillator arrays that are packaged in modules with photodetectors to measure the light pulses from respective scintillation events. For example, the light from respective elements of a scintillator crystal array can be shared among multiple photomultiplier tubes (PMTs) or can be detected by silicon photomultipliers (SiPMs) having a one-to-one correspondence with the elements of a scintillator crystal array.

To reconstruct the spatio-temporal distribution of the tracer via tomographic reconstruction principles, each detected event is characterized for its energy (i.e., amount of light generated), its location, and its timing. By detecting the two gamma rays, and drawing a line between their locations, i.e., the line-of-response (LOR), one can determine the likely location of the original disintegration. The timing information can also be used to determine a statistical distribution along the LOR for the annihilation based on a time-of-flight (TOF) information of the two gamma rays. By accumulating a large number of LORs, tomographic reconstruction can be performed to determine a volumetric image of the spatial distribution of radioactivity (e.g., tracer density) within the patient.

Single-photon emission computed tomography (SPECT) is similar to PET except a collimator is used to restrict the solid angle of gamma rays incident on the respective detector elements (e.g., the respective elements in the scintillator crystal array), making reconstruction possible using single gamma ray detection events as opposed to requiring coincidences to determine a LOR.

In addition to position information (e.g., the LOR) and timing information (e.g., the TOF), detectors in PET and SPECT systems can also acquire and use energy information in the image reconstruction process. However, energy measurements can deviate from an ideal linear response due to non-linearities in the measurement process and/or practical considerations related to, e.g., light/charge sharing among channels during a multi-channel gamma-ray detection (e.g., due to the gamma ray energy being absorbed in multiple detectors/channels as can happen due to Compton scattering). Accordingly, improved techniques are desired to correct energy measurements in pixelated gamma-ray detectors.

BRIEF DESCRIPTION OF THE DRAWINGS

A more complete understanding of this disclosure is provided by reference to the following detailed description when considered in connection with the accompanying drawings, wherein:

FIG. 7A shows, for a single-channel detection event, an example of energy distribution among pixels (i.e., crystal elements) in the absence of signal sharing among the pixels;

FIG. 7B shows, for the single-channel detection event, an example of energy distribution among the pixels in the presence of 5% light sharing among the pixels;

FIG. 8A shows, for a multi-channel detection event, an example of energy distribution among pixels (i.e., crystal elements) in the absence of signal sharing among the pixels;

FIG. 8B shows, for the multi-channel detection event, an example of energy distribution among the pixels in the presence of 5% light sharing among the pixels;

DETAILED DESCRIPTION

Figure 1:
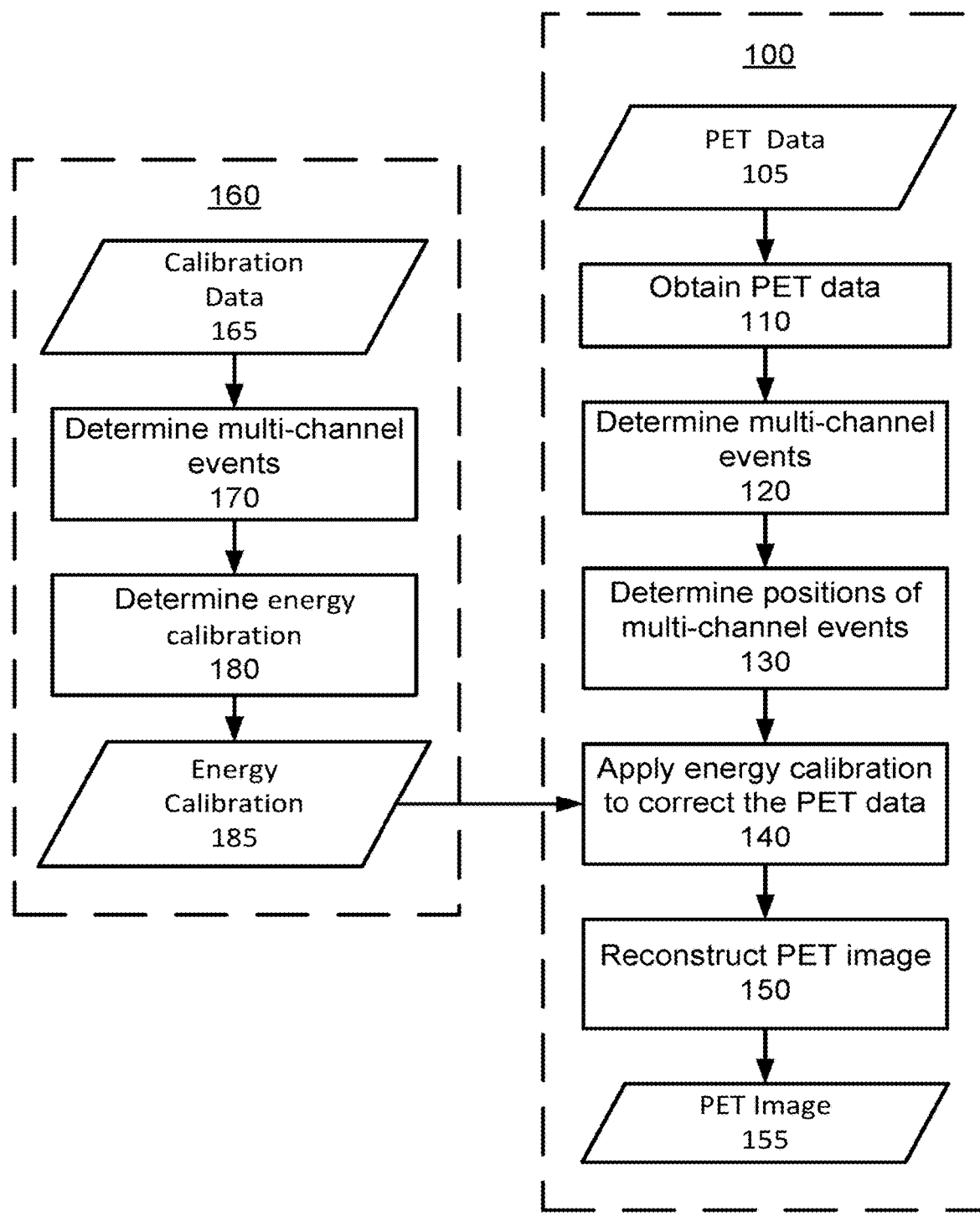
FIG. 1 shows examples of flow diagrams for a method 160 to generate energy calibrations and a method 100 using the energy calibrations to correct energy measurements, according to one implementation.

As discussed above, image reconstruction for positron emission tomography (PET) and/or single-photon emission computed tomography (SPECT) can be performed using position, time, and/or energy information. These energy measurements can deviate from an ideal linear response due to various practical considerations. For example, non-linearities can arise in the measurement process as a result of using the time-over-threshold as a surrogate quantity to represent the energy. Further, multi-channel detection of a gamma-ray, such as occurs when a gamma ray undergoes Compton scattering giving rise to two (or more) signals for a single gamma ray, can be partially corrected for by summing the energy values of the two (or more) signals of the single gamma. Nevertheless, due to light sharing and/or charge sharing, when adjacent channels are involved in a multi-channel event the summed energy can deviate from the energy that would be measured if the gamma ray were detected as a single-channel event (e.g., without Compton scattering). Accordingly, the methods and apparatus described apply improved approaches and techniques to correct energy measurements to generate corrected energy values that are substantially linear.

As discussed above, most commercial positron emission tomography (PET) systems use arrays of scintillator crystals to detect gamma rays having energies of 511 keV that are generated by positron-electron annihilation. These PET systems can provide both energy and position information. Sometimes the energy of a gamma ray can be shared by two crystals due to inter-crystal scattering (e.g., Compton scattering). When the energy from a single gamma ray is detected at more than one crystal/channel, the detection event can be referred to as "multi-channel detection." The total energy of a scattering event can be recovered by adding individual energies from all involved crystals (the respective crystals and their corresponding photodetectors, amplifiers and electronics can also be referred to as "channels"). The summing can be realized either through analogue or digital methods depending on the choice of readout and electronics.

The energy deposited in a crystal can be converted to an electrical signal, and the electrical signal can then be digitized. This digitization process can be performed by various methods. Among the methods for digitizing the energy measurements of gamma rays, the time-over-threshold (TOT) method has the advantages of being very cost effective and can be easily applied to applications requiring high channel density. Although the TOT value is monotonically related to the actually energy absorbed in a given channel, the relation between the TOT and the actual energy can deviate from being perfectly linear. Certain implementations of the methods described herein correct for these deviations from linearity.

As used herein, the term "energy" is not restricted to mean a calibrated energy that is linearly related to the actual or true energy. In general, the term "energy", as used herein, specifies an energy coordinate that represents and is related monotonically to the actual or true energy. Thus, the term "energy" does not necessarily refer to actual or true energy, unless context clearly indicates otherwise. For example, when the summing of energies is discussed herein, this summing can be performed on "energy coordinates," rather than a calibrated value that is linearly related to the actual energy. Because the relation of the measured/raw energy $E_{raw}$ (i.e., "energy coordinates") can be related to the true energy $E_{true}$ by a nonlinear function $E_{raw}=f(E_{true})$, the sum of two measured energies $f(E_1)$ and $f(E_2)$ from two-channel detection (i.e., $E_1+E_2=E_{Total}$, wherein $E_{Total}$ is the true energy of the incident, e.g., 511 keV) does not equal the measured/raw energy for an equivalent single-channel detection, i.e., $f(E_1)+f(E_2) \neq f(E_{Total})=f(E_1+E_2)$. Accordingly, to accurately compare the energies of multi-channel detections with signal-channel detections, an energy calibration and correction is applied to the summed energies of the multi-channel detections.

Further, better performance at very high count rates can be achieved when the number of read-out channels is very high, thereby reducing dead-time and pile-up effects. An example is one-to-one readout of crystals, meaning that each crystal is coupled directly to only one photodetector. In this case, the crystals are optically isolated, such that the gamma-ray energy converted into scintillation photons is maintained within the crystal element that absorbed the gamma-ray energy. Frequently, the optical isolation is imperfect, and, even with the best light-blocking materials between crystal elements, the optical isolation still permits a small amount of optical cross-talk between adjacent crystals. Accordingly, the methods described herein provide an energy calibration accounting for differences in energies measured in multi-channel detection that exhibit cross-talk between channels.

Figure 2A:
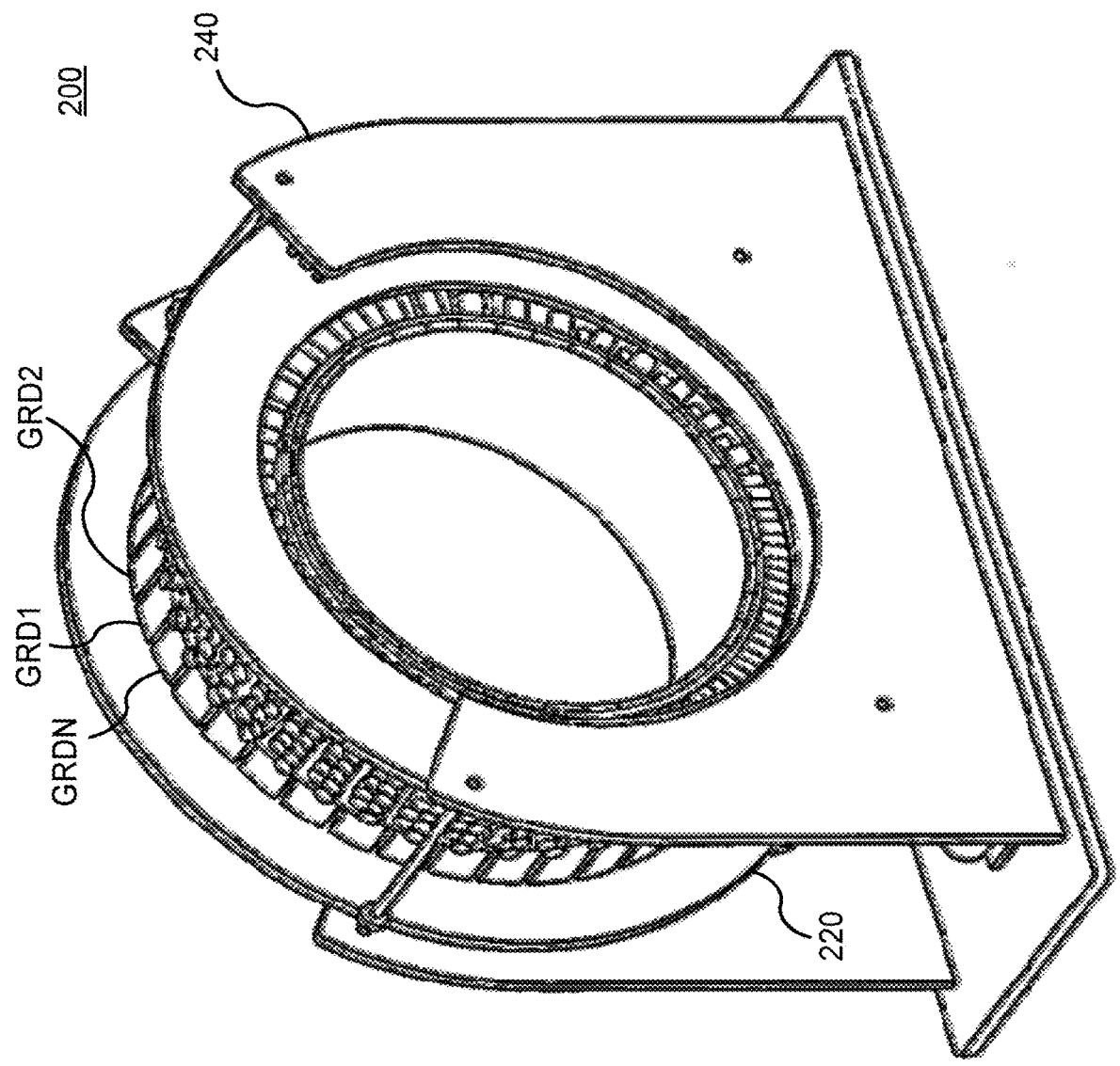
FIG. 2A shows a perspective view of a positron-emission tomography (PET) scanner, according to one implementation.
Figure 2B:
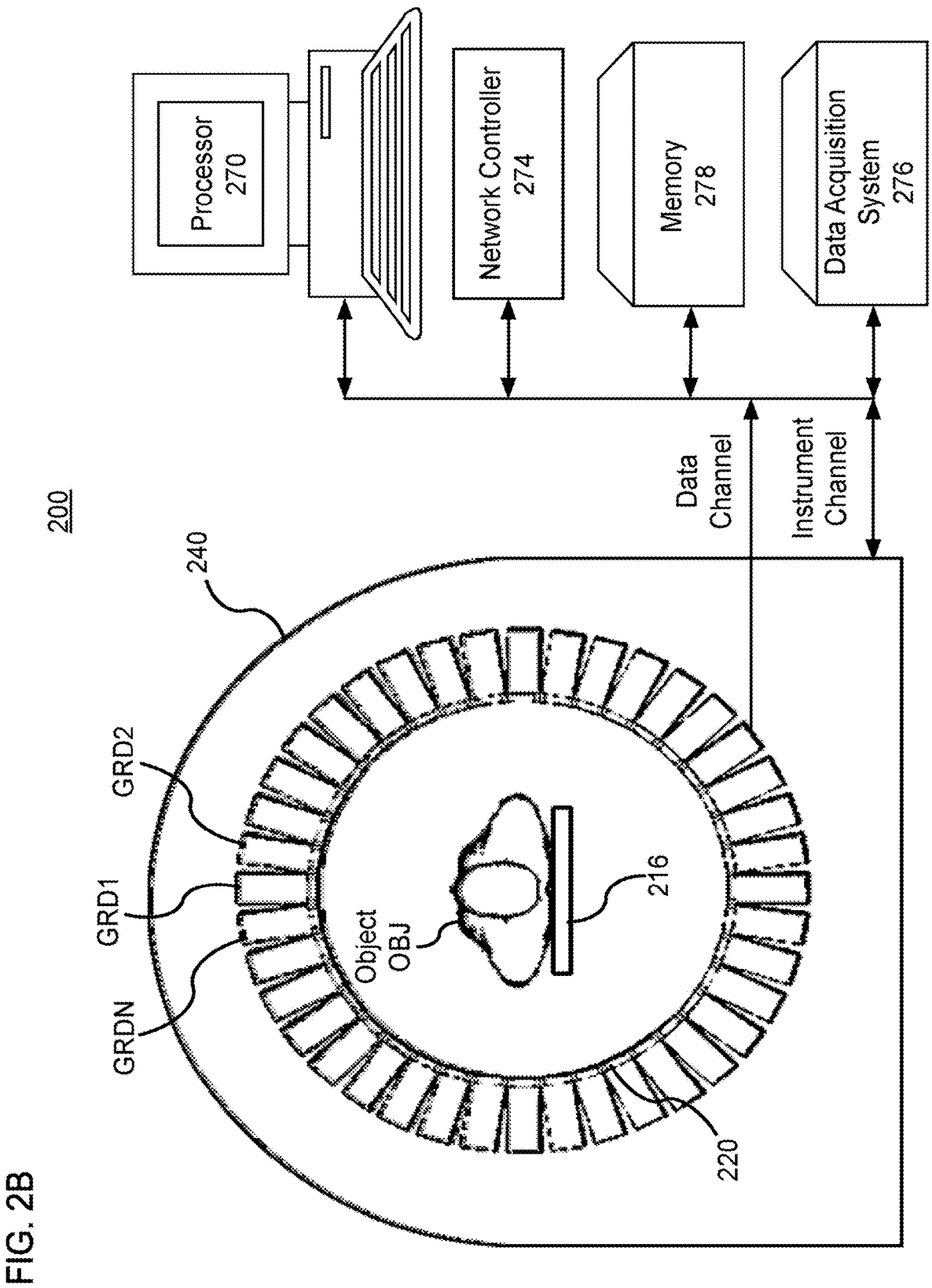
FIG. 2B shows a schematic view of the PET scanner, according to one implementation.

Referring now to the drawings, wherein like reference numerals designate identical or corresponding parts throughout the several views, FIG. 1 shows a non-limiting example of a flow diagram of a method 100 for correcting energy measurements in PET data 105, and shows a non-limiting example of a flow diagram of a method 160 for determining an energy calibration to be used in method 100 to correct the energy measurements in the PET data 105. Further, FIGS. 2A and 2B show a non-limiting example of a PET scanner that can be used to perform the methods 100 and 160.

FIG. 1 shows the flow charts of the methods 100 and 160 performing an energy calibration of emission data to account for multi-channel events to correct the PET data 105, and then reconstructing a PET image 155 from the calibrated emission data. The methods 100 and 160 can be performed by the PET imaging apparatus 200 shown in FIGS. 2A and 2B, such as a PET system.

At step 110, the processing circuitry is configured to obtain and pre-process emission data 105 from a positron-emission source. For example, the PET scanner 200 can obtain emission data 105 representing energy data and position data of detection events corresponding to coincidence pairs from respective positron emissions occurring in an object OBJ. The detection events can be detected at a plurality of detector elements and modules, and each of the detector modules can include two or more channels (i.e., detector elements).

At step 120, the processing circuitry is configured to select from the emission data 105 multi-channel detection events, and then group them by event. That is, each group corresponds a single primary gamma ray, such that for first-order scatter each group will include two hits (i.e., the hit of the first crystal that absorbed part of the primary gamma ray and emitted the remaining energy as the scattered gamma ray and the hit of the second crystal, which absorbed the scattered gamma ray). Similarly, each group for a second-order scatter event will include three hits (i.e., one for the primary gamma ray and two for each of the two scatter gamma rays), and so forth (e.g., four hits in groups corresponding to third-order scatter, etc.). Multi-channel events can be selected, e.g., based on the detection signals' proximity in time and space, based on the sum of the energies of the signals, and any combination of the summed energies and the detection signals' proximity in time and space. For example, if the gamma-ray source has a known energy (e.g., 511 keV for gamma rays from positron annihilation), then the more closely the signals sum to the known energy the more likely the signals correspond to a same multi-channel event. Further, signals occurring closer together in time are more likely to correspond to a same multi-channel event, and signals occurring closer together in space are more likely to correspond to a same multi-channel event. Moreover, when all three of the above conditions (i.e., energy, time, and space) are all satisfied, then the signals are even more likely to correspond to a same multi-channel event. Thus, the processing to group signals into multi-channel events can be performed using a multivariate statistical analysis.

The processing circuitry can be additionally configured to determine whether the two or more channels of the particular detector module includes more than two channels (e.g., when second-order or higher-orders of Compton scattering occur). In certain implementations, only first-order scatter is used for timing calibrations, and multi-channel events for higher-order scatter are discarded. In other implementations, multi-channel events for both first-order scatter and higher-order scatter are used for the timing calibrations. Consequently, the processing circuitry can be configured to either decompose the data of the two or more channels into corresponding two-channel events, or to discard the multi-channel events entirely.

At step 130, the position data is determined for the multi-channel events. Herein, the term "position data" or more simply "position" can refer to an absolute position in three-dimensional space, a two-dimensional coordinate within a given detector module, or refer to a crystal identity (ID) such as an index that uniquely identifies the individual crystal elements within a detector array module, etc. For example, the crystal ID, although not an absolute location in three-dimensional Euclidean space, is sufficient to label the physical location where a detection event occurred. Thus, the "position data" and "position" is not restricted to meaning an absolute position that has been calibrated to correspond to a rectilinear space, rather the terms "position data" and "position" can be coordinates that designate/identify spatially distinct crystal elements.

In the case a first-order scatter, a group of two hits at the detector elements are selected as being the multi-channel event. Each of the hits being a detection signal of a detector channel including quantities for a position (x) and energy (E) and in certain implementations time (t). As such, if there are two hits, there will be a first and second time (i.e., $t_1$ and $t_2$), a first and second position (i.e., $x_1$ and $x_2$), and a first and second energy (i.e., $E_1$ and $E_2$). Any known method can be used to determine the position of the multi-channel event. For example, an energy weighted two-dimensional (2D) coordinate can be calculated for each multi-channel event using, e.g., the formula $$\vec{X} = \frac{\sum_i^n \vec{x}_i E_i^w}{\sum_i^n E_i^w},$$

wherein $\vec{x}_i$ is the central coordinates of channel i, $E_i$ is the energy of channel i (e.g., in certain implementations $E_1$ can be a non-linearity calibrated energy, or in other implementations $E_i$ can be a raw energy value), w can be a power/exponent applied to the energy $E_i$ to provide the energy weight $E_i^w$, and w can be any value except for 0. As discussed below, the central coordinates $\vec{x}_i$ for the $i^{th}$ channel can be obtained based on a crystal identity (ID).

At step 140, the energy calibrations 185 are applied to the PET data to generate corrected PET data, as discussed below. In various implementations, these energy calibrations 185 can include a correction to linearize a time-over-threshold (TOT) value with respect to energy, a correction for energy differences between single-channel events and multi-channel events, or a combination of these corrections.

In certain implementations, the energy values of the PET data 105 are used to select for image reconstruction only those coincidence counts with energies in a predefined window (e.g., an energy window around 511 keV). In this case, rather than applying a scaling the multi-channel energies and then applying a window around 511 keV to the shifted/scaled energies, an inverse scaling can be applied to the window and then the shifted window can be applied to the unshifted multi-channel energies. This way, only the window requires scaling, and the shifted window for a given block and order of scatter/multiplicity can be used to each of the multi-channel event in that block and channel multiplicity. Different calibrations can apply to different blocks and to different channel multiplicities within a given block. The channel multiplicity refers the number of channels involved in a multi-channel detection. For example, first-order Compton scatter can be detected at two channels corresponding to a multiplicity of two. Second-order Compton scatter can be detected at three channels corresponding to a multiplicity of three, and so forth.

A different energy calibration/shift can apply for each block and for each multiplicity within a given block. And these respective energy calibrations/shifts can be stored in a look-up table. Even though there can be many blocks and multiplicities, there can be many multi-channel events per multiplicity in a given block. Thus, the number of calculations can be reduced by applying the energy shift to the window for a given multiplicity and block, rather than applying the energy shift to each of the many multi-channel events corresponding to the given multiplicity and block.

At step 150, a PET image 155 is reconstructed from the correct PET data using any known reconstruction method. For example, the PET data 105 can be used to reconstruct an image of radioactivity level (e.g., tracer density) as a function of voxel position. The image reconstruction can be performed using a back-projection method, a filtered back-projection method, a Fourier-transform-based image reconstruction method, an iterative image reconstruction method, a matrix-inversion image reconstruction method, a statistical image reconstruction method, a list-mode method, or other reconstruction method or combination thereof, as would be understood as a person of ordinary skill in the art. For example, the initial PET image can be reconstructed using an ordered subset expectation maximization (OS-EM) algorithm that is initialized with an FBP reconstructed PET image.

Method 160 generates the energy calibration 185 from calibration data 165. The calibration data 165 can be gamma ray measurements generated by the detector elements of the PET system 200. The calibration data 165 can be but does not have to be generated as coincidence counts from a positron emission source. Alternatively, the calibration data 165 can be generated using one or more sources of unpaired gamma rays (referred to as "unpaired sources") that produce different gamma ray energies.

For example, the calibration data 165 can be generated using an unpaired source having one or more pieces of cesium isotope 137 (Cs-137), having a half-life of approximately 30 years and producing gamma rays with energies of 662 keV. These pieces of Cs-137 can be arranged to create an approximately uniform flux density of gamma rays within the beam. In certain implementations, the beam can be a cone beam or can isotopically radiate into all $4\pi$ steradians. The gamma rays with energies of 662 keV produced by the Cs-137 are higher than the 511 keV gamma rays produced by positron-emission radiation sources. Instead of multiple pieces, a substantially uniform distributed source could be used (commonly known as a "flood source"). Other gamma ray sources that can be used include, e.g., (i) cobalt isotope 60 (Co-60 with a half-life of 5.3 years and gamma-ray energies of 1.17 MeV and 1.33 MeV);

(ii) germanium isotope 68 (Ge-68 with a half-life of 0.74 years and gamma-ray energy of 511 keV); and (iii) sodium isotope 22 (Na-22 with a half-life of 2.6 years and gamma-ray energies of 511 keV and 1.275 MeV).

When the energy of the gamma rays produced by a given source are greater than the 511 keV energy generated by positron emission, these higher gamma-ray energies can result in the energy deposited in the various detector elements during Compton scattering covering a large range of energies both below and above 511 keV, allowing for more complete calibration of the mapping from TOT values to energies.

At step 170, the calibration data 165 is sorted into multi-channel events and single-channel events. This sorting and filtering of the multi-channel events from the total set of the calibration data 165 can be performed using methods similar to those described in step 120 of method 100.

At step 180, the calibration data 165 is used to generate the energy calibration 185. As discussed above, the energy calibration 185 can include TOT nonlinearity corrections, multi-channel corrections, or both. For example, the energy calibration 185 can be a lookup table indexed by the positions/identities (IDs) of respective detector elements to obtain parameters of an equation expressing a non-linear correction. Accordingly, the parameterization of the energy calibration can be performed on a detector element by detector element basis. For example, as discussed below, an energy shift $\Delta E$ incurred in multi-channel detection due to charge sharing can be parameterized by the expression $$\Delta E(x, \delta_1, \delta_2) = E(x, \delta_1, \delta_2) - E(1, \delta_1, \delta_2)$$
$$= E_0(x(1 - 3\delta_1) + (1-x)(1 - 3\delta_2)) - E_0(1 - 4\delta_1)$$
$$= E_0(\delta_1 + 3x(\delta_2 - \delta_1)),$$

wherein x is the fraction of energy left in crystal 1, and $\delta_1$ and $\delta_2$ are the optical cross-talk of two crystals with neighbouring crystals. In this parameterization, the energy shift is proportional to the level of optical cross talk. In certain crystal arrays, $\delta_1$ and $\delta_2$ may also depend on the direction of sharing (e.g., the light-sharing can be asymmetric). Thus, when the level of cross talks varies from crystal to crystal, the energy shift $\Delta E$ also changes as a function energy sharing. In some implementations, the level of optical cross-talk and the amount of the energy shift $\Delta E$ can depend on a position of a crystal element within a detector module, as discussed below.

Now, a description is provided of a non-limiting example of a PET system 200 that is configured with detector modules (i.e., gamma-ray detectors (GRD)) arranged in an annular shape. Each of the detector modules can include several arrays of detector elements. The GRDs include scintillator crystal arrays for converting the gamma rays into scintillation photons (e.g., at optical, infrared, and ultraviolet wavelengths), which are detected by photodetectors. In the non-limiting example illustrated in FIGS. 2A and 2B, the photodetectors are photomultiplier tubes (PMTs) that are much bigger than the respective scintillator crystal elements. In one preferred embodiment, the photodetectors are silicon photomultipliers (SiPMs) that can have a detection cross-section that approximates the cross-sectional area of the individual scintillator crystal elements, creating a one-to-one correspondence between the crystals and the photodetectors. This embodiment is illustrated by the non-limiting example shown in FIGS. 3C and 5. If the photodetectors are larger than the crystals, such that a single photodetector is used to detect the optical signals from multiple crystals, then Anger arithmetic can be used to determine the positions. However, Anger arithmetic is not necessarily required when there is a one-to-one correspondence between the crystals and the photodetectors.

FIGS. 2A and 2B show a non-limiting example of a PET scanner 200 that can implement the methods 100 and 160. The PET scanner 200 includes a number of gamma-ray detectors (GRDs) (e.g., GRD1, GRD2, through GRDN) that are each configured as rectangular detector modules. According to one implementation, the detector ring includes 40 GRDs. In another implementation, there are 48 GRDs, and the higher number of GRDs is used to create a larger bore size for the PET scanner 200.

Each GRD can include a two-dimensional array of individual detector crystals, which absorb gamma radiation and emit scintillation photons. The scintillation photons can be detected by a two-dimensional array of photomultiplier tubes (PMTs) that are also arranged in the GRD. A light guide can be disposed between the array of detector crystals and the PMTs.

Alternatively, the scintillation photons can be detected by an array a silicon photomultipliers (SiPMs), and each individual detector crystals can have a respective SiPM.

Each photodetector (e.g., PMT or SiPM) can produce an analog signal that indicates when scintillation events occur, and an energy of the gamma ray producing the detection event. Moreover, the photons emitted from one detector crystal can be detected by more than one photodetector, and, based on the analog signal produced at each photodetector, the detector crystal corresponding to the detection event can be determined using Anger logic and crystal decoding, for example.

FIG. 2B shows a schematic view of a PET scanner system having gamma-ray (gamma-ray) photon counting detectors (GRDs) arranged to detect gamma-rays emitted from an object OBJ. The GRDs can measure the timing, position, and energy corresponding to each gamma-ray detection. In one implementation, the gamma-ray detectors are arranged in a ring, as shown in FIGS. 2A and 2B. The detector crystals can be scintillator crystals, which have individual scintillator elements arranged in a two-dimensional array and the scintillator elements can be any known scintillating material. The PMTs can be arranged such that light from each scintillator element is detected by multiple PMTs to enable Anger arithmetic and crystal decoding of scintillation event.

FIG. 2B shows an example of the arrangement of the PET scanner 200, in which the object OBI to be imaged rests on a table 216 and the GRD modules GRD1 through GRDN are arranged circumferentially around the object OBJ and the table 216. The GRDs can be fixedly connected to a circular component 220 that is fixedly connected to the gantry 240. The gantry 240 houses many parts of the PET imager. The gantry 240 of the PET imager also includes an open aperture through which the object OBJ and the table 216 can pass, and gamma-rays emitted in opposite directions from the object OBJ due to an annihilation event can be detected by the GRDs and timing and energy information can be used to determine coincidences for gamma-ray pairs.

In FIG. 2B, circuitry and hardware is also shown for acquiring, storing, processing, and distributing gamma-ray detection data. The circuitry and hardware include: a processor 270, a network controller 274, a memory 278, and a data acquisition system (DAS) 276. The PET imager also includes a data channel that routes detection measurement results from the GRDs to the DAS 276, a processor 270, a memory 278, and a network controller 274. The data acquisition system 276 can control the acquisition, digitization, and routing of the detection data from the detectors. In one implementation, the DAS 276 controls the movement of the bed 216. The processor 270 performs functions including reconstructing images from the detection data, pre-reconstruction processing of the detection data, and post-reconstruction processing of the image data, as discussed herein.

The processor 270 can be configured to perform various steps of methods 100 and 160 described herein and variations thereof. The processor 270 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the processor 270 can execute a computer program including a set of computer-readable instructions that perform various steps of methods 100 and 160, the program being stored in any of the above-described non-transitory electronic memories and/or a hard disk drive, CD, DVD, FLASH drive or any other known storage media.

Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

The memory 278 can be a hard disk drive, CD-ROM drive, DVD drive, FLASH drive, RAM, ROM or any other electronic storage known in the art.

The network controller 274, such as an Intel Ethernet PRO network interface card from Intel Corporation of America, can interface between the various parts of the PET imager. Additionally, the network controller 274 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

Figure 3A:
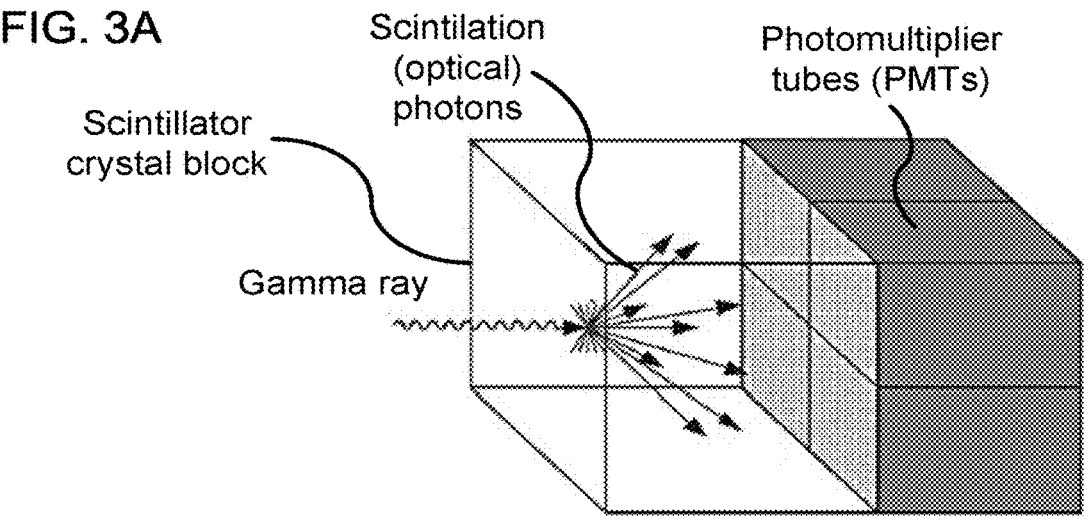
FIG. 3A shows a diagram of a gamma ray detector module having a single crystal and photomultiplier tubes (PMTs), according to one implementation.
Figure 3B:
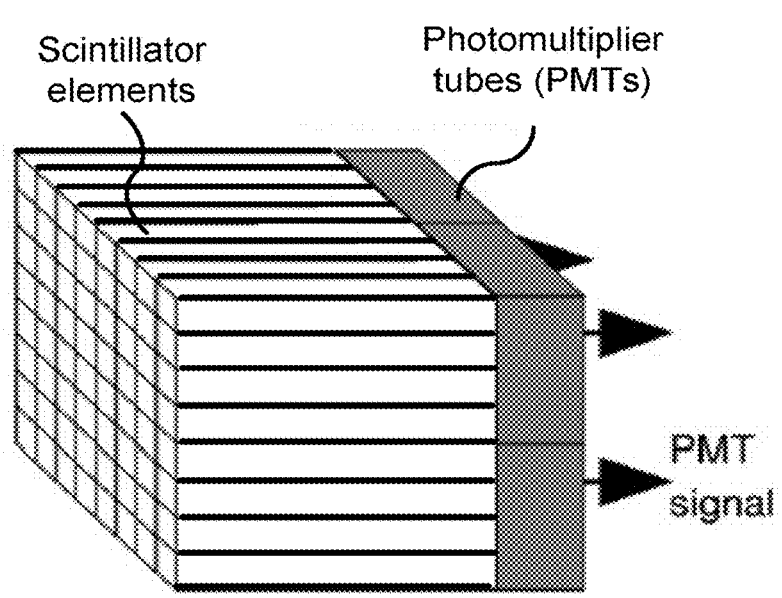
FIG. 3B shows a diagram of a gamma ray detector module having multiple scintillator crystal elements arranged as an array and using PMTs as photodetectors, according to one implementation.
Figure 3C:
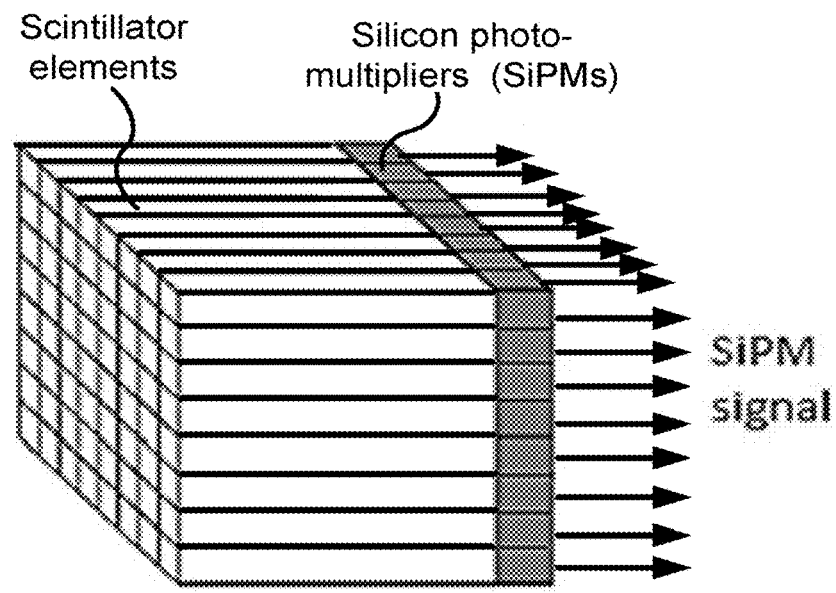
FIG. 3C shows a diagram of a gamma ray detector module having multiple scintillator crystal elements arranged as an array and using silicon photomultipliers (SiPMs) as photodetectors, according to one implementation.

FIGS. 3A, 3B, and 3C show several non-limiting implementations of a gamma ray detector (also referred to as a gamma camera). In FIG. 3A, the scintillator crystal is a single monolithic block, and the location of the scintillation event converting the gamma ray photon into secondary photons that can be detected by an array of photodetectors, which are illustrated here as photomultiplier tubes (PMTs). The location of the scintillation event can be determined using Anger arithmetic.

In FIG. 3B, the scintillator is cut into a periodic array of separate crystals separated and optically isolated by reflective barriers between the individual elements of the crystal array. This optical isolation between crystals in the block can be imperfect allowing some light sharing between adjacent crystals. When the photodetectors are PMTs, the light sharing between adjacent crystals can be small compared to light sharing that occurs after exiting the crystals, in which case, scintillation events can be distinguished between individual elements of the array using Anger arithmetic to approximately determine locations and then using a floodmap calibration to generate a lookup table mapping the approximate locations calculated using Anger arithmetic to respective indices of the crystal array.

In FIG. 3C, the light from each crystal element is detected by a respective silicon photomultiplier (SiPM). With each crystal having its own photodetector, the light sharing among photodetectors can be reduced. Further, each crystal having its own photodetector can result in enhanced resolution by enabling discrimination between simultaneous scintillation events occurring at different crystals within a single detection module (e.g., discriminating Compton scattering among adjacent crystals).

For many years, the most commonly used photo detectors for PET has been PMTs, which are vacuum tubes having a photo-cathode material with a work function that allows the conversion of incoming light into photoelectrons that are accelerated through an applied electric field and amplified by interacting with a cascade of dynodes. The resulting electrical current is proportionate to the number of initial scintillation photons and therefore to the energy deposited in the scintillation crystal by the gamma ray.

By segmenting the scintillator blocks (e.g., using many small SiPMs or exploiting the properties of position sensitive PMTs, e.g., using Anger arithmetic) the location of the photon detection can be determined. In FIGS. 3B and 3C small individual scintillation crystals that are a few millimeters in size are tightly packed into blocks/modules, which can be coupled to multiple photodetectors. In Anger arithmetic, the interaction location of the annihilation photon is determined by comparing the relative signals in the photodetectors, which is determined by relative light sharing due the spread-out scintillation photon signals. The calculated location then determines the crystal element to which the photon is assigned based on the floodmap calibrated lookup table.

Figure 4A:
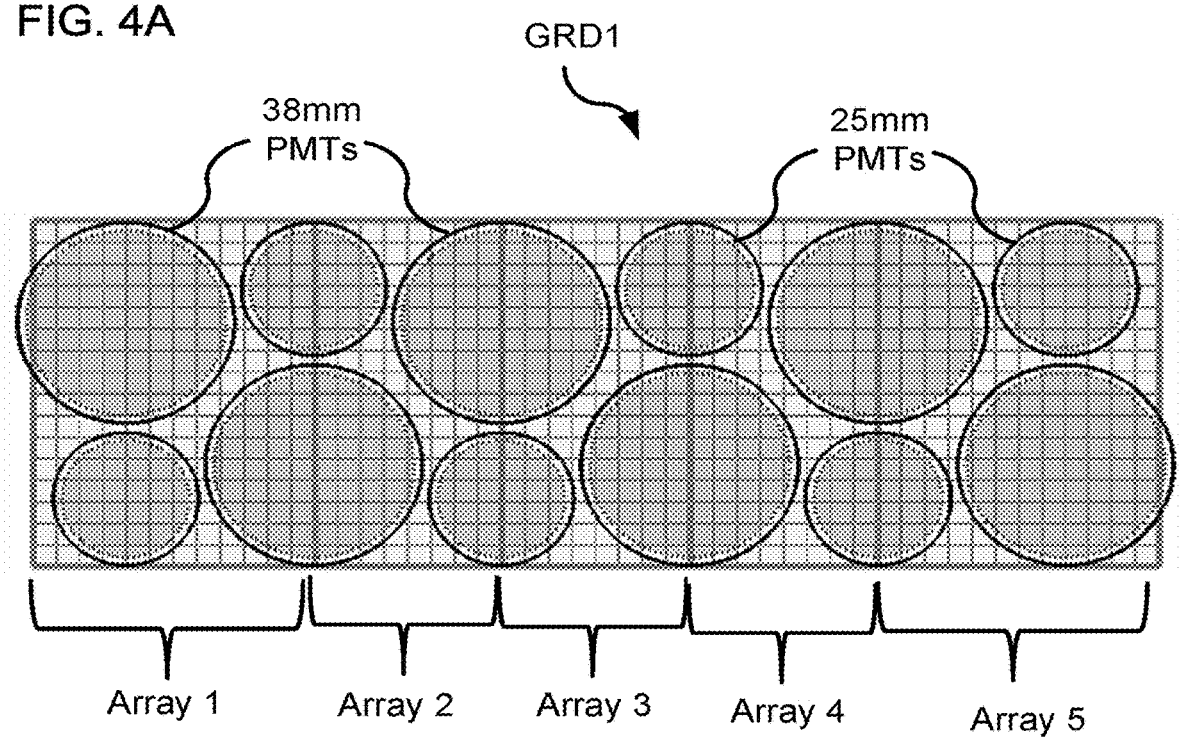
FIG. 4A shows a top view of a gamma-ray detector (GRD) module using PMTs, according to one implementation.
Figure 4B:
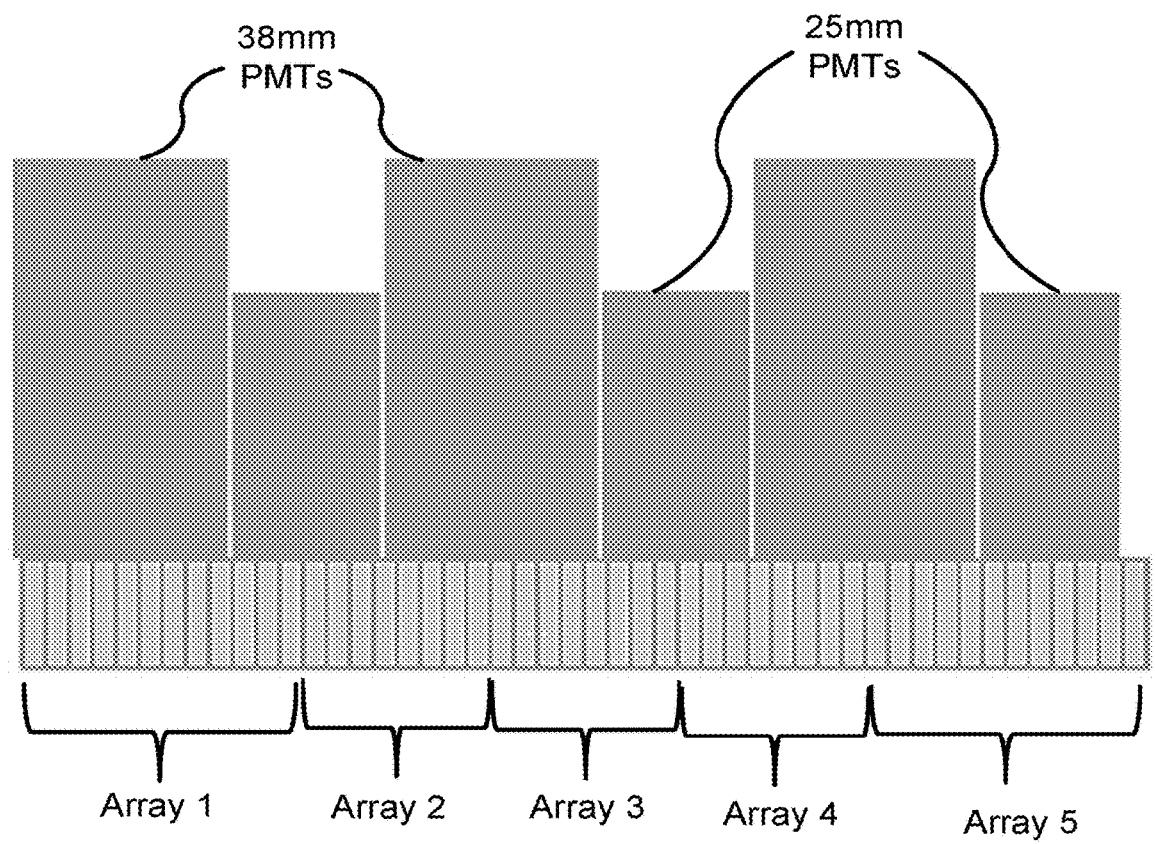
FIG. 4B shows a side view of the PMT-GRD module, according to one implementation.
Figure 4C:
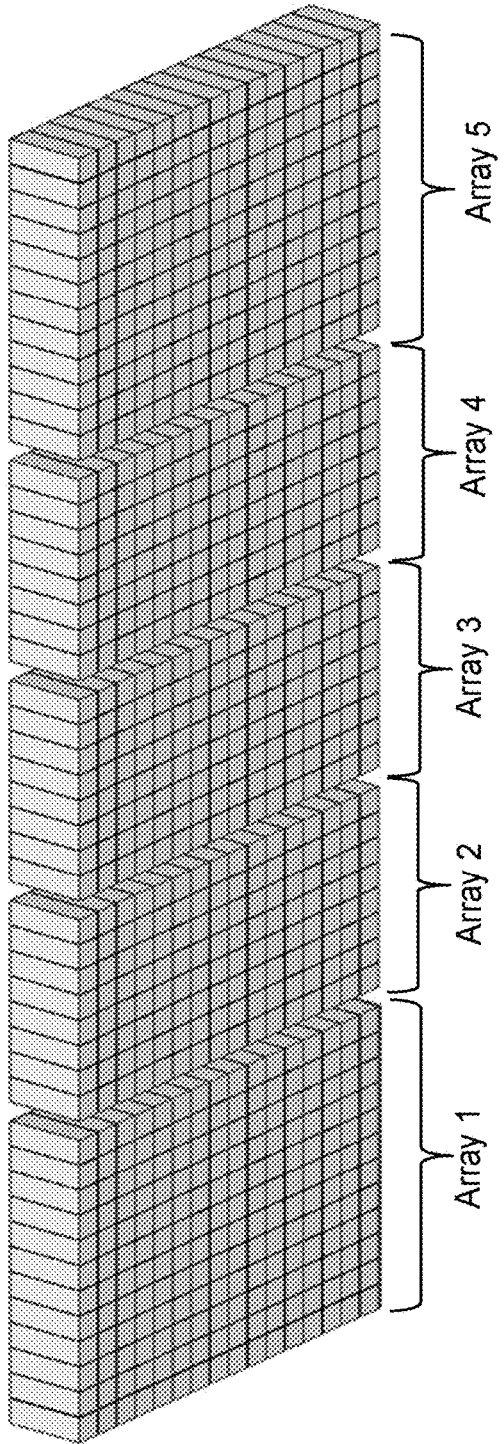
FIG. 4C shows a perspective view of a series of scintillator crystal arrays, according to one implementation.
Figure 4D:
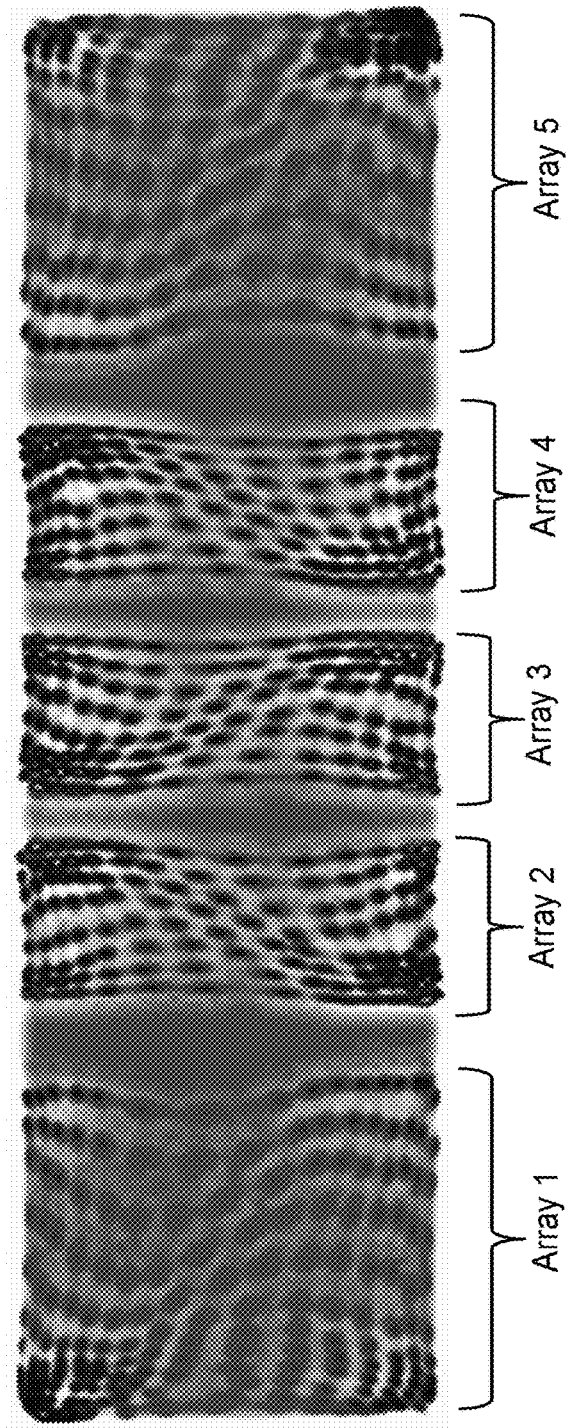
FIG. 4D shows a top view of a floodmap calibration of counts as a function of position calculated using Anger logic, according to one implementation.

FIGS. 4A and 4B respectively show top and side views of a GRD detector module using PMTs as the photodetectors. The GRD uses two different sizes of PMTs (25 mm PMTs and 38 mm PMTs) to cover a larger percentage of the area of the scintillator crystal arrays than can be achieved using PMTs all of the same size. Array 1 and array 5 are 11 pixels by 16 pixels, and array 2, array 3, and array 4 are 8 pixels by 16 pixels. FIG. 4C shows a prospective view of the five crystal arrays, and FIG. 4D shows a floodmap calibration of a histogram of counts as a function of the approximate positions calculated using Anger arithmetic. Because Anger arithmetic generates approximate positions, the local maxima of the histogram can be identified as corresponding to the centers of respective crystal elements, and then stored as a position calibration in a lookup table that is used when determining the position information (e.g., $\vec{x}_i$ of the central coordinates of channel i).

Figure 5:
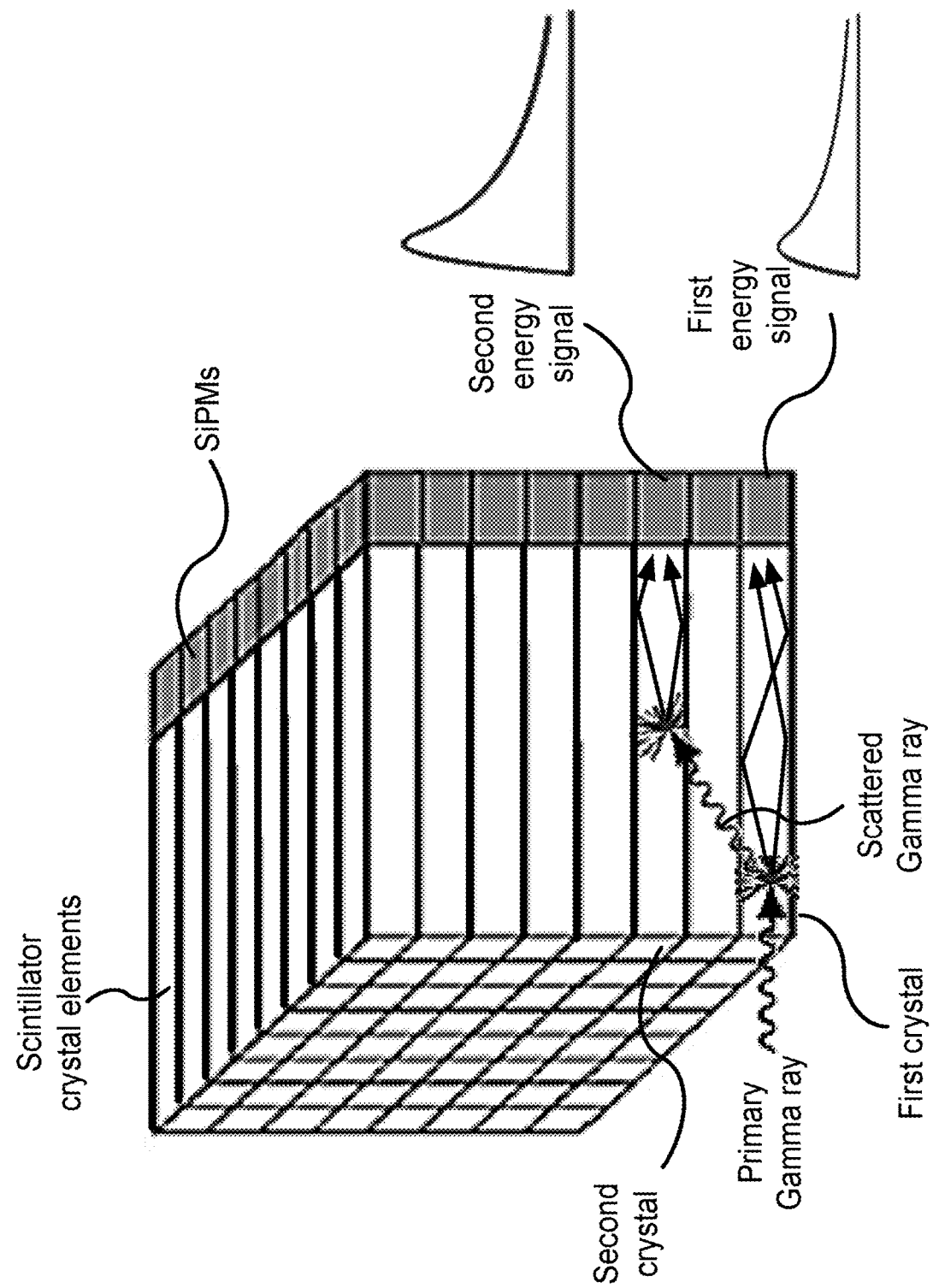
FIG. 5 shows an example of Compton scattering resulting in two energy signals from a single primary gamma ray, according to certain aspects of the present disclosure.

FIG. 5 shows a non-limiting example of an incident gamma ray undergoing Compton scatter in a first crystal resulting in the remaining energy being deposited in a second crystal. The first and second crystals then respectively produce secondary photons via photoelectric absorption resulting in the corresponding SiPMs generating the first and second energy signals. The scatter angle is small, and the energy in the first energy signal is less than the energy in the second energy signal. Even if the shapes of the first and second pulses are the same and differ on their magnitudes, the two signals can be registered as occurring at different times due to a time-walk offset that arises when the arrival time is based on when the rising edge of the pulse exceeds a predetermined value, as illustrated in FIG. 5.

Figure 6A:
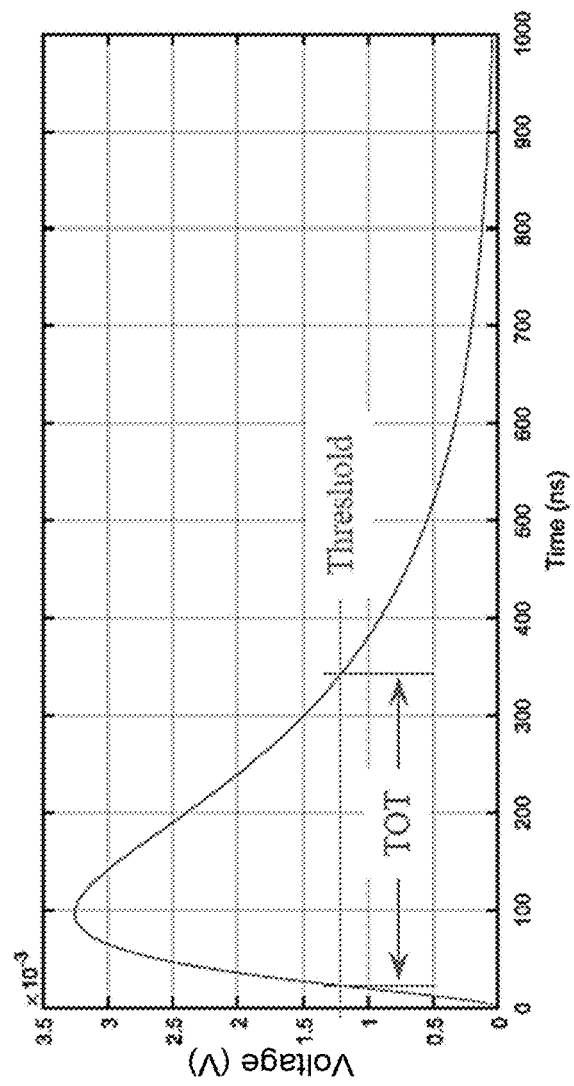
FIG. 6A shows a plot of a time-over-threshold (TOT) measurement, according to one implementation.
Figure 6B:
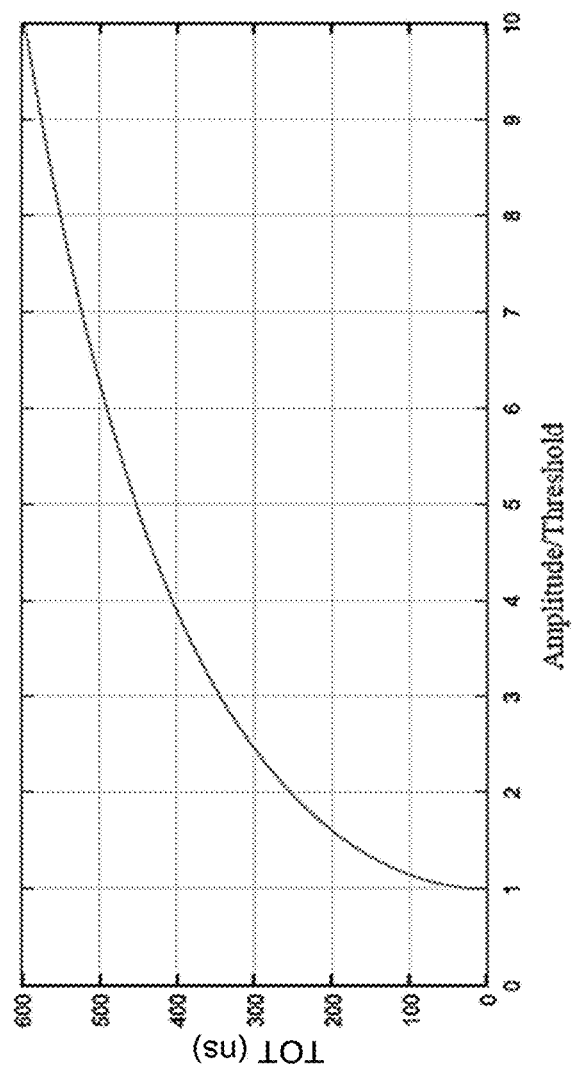
FIG. 6B shows, for a given pulse shape, a plot of the TOT as a function of the ratio peak height to the threshold, according to one implementation.

FIGS. 6A and 6B show plots for a TOT nonlinearity correction, which can be calibrated in step 180 and applied in step 140. FIG. 6A plots, as a function of time, the voltage of a pulse from the detection of a gamma ray. Further, FIG. 6A shows a predefined threshold at about 1.2 millivolts, and the duration of time that the pulse exceeds this threshold is the TOT value. As illustrated in FIG. 6B, the TOT value is monotonically related to the energy of the detected gamma ray, which can be represented by the area under the curve of the pulse, or by the amplitude of the pulse, when the pulse shape remains undistorted by changes in the pulse magnitude. For signals below the threshold no hit is registered.

A function modeling the plot in FIG. 6B can be generated in step 180 from the calibration data using one of many methods. For example, using only the single-channel events, different energy sources with known energy values for the gamma rays can be used to determine the TOT value corresponding to different energy values, and a function (e.g., a shifted square root) can be curve fit to these points.

Also, the empirically measured data can be supplemented at lower gamma ray energies using the detections of scattered gamma rays from Compton scattering, which have energies less than the incident/initial gamma ray. The energies of the Compton scattering detections can be determined based on the area under the curve or the amplitude of the pulse. This calibration can be performed once and stored in memory, and then be recalled from memory when a PET scan is being performed or processed. The described method of calibration is a non-limiting example, and other methods of calibrating the mapping from TOT values to energies can be used without departing from the spirit of the methods and apparatuses described herein.

The Time-over-Threshold (TOT) method estimates the amplitude of a signal by measuring the total time of a signal over given threshold. The measured time is then translated back to amplitude through a non-linear conversion (e.g., the mapping function shown in FIG. 6B). Due to the presence of a threshold, any amplitude blow the threshold will be reported as zero (i.e., not hit). When TOT technique is apply to detector array with non-negligible optical cross talk, the reported total energy will shift when the incident gamma's energy is shared by two crystals due to scattering.

Figures 7A, 7B:
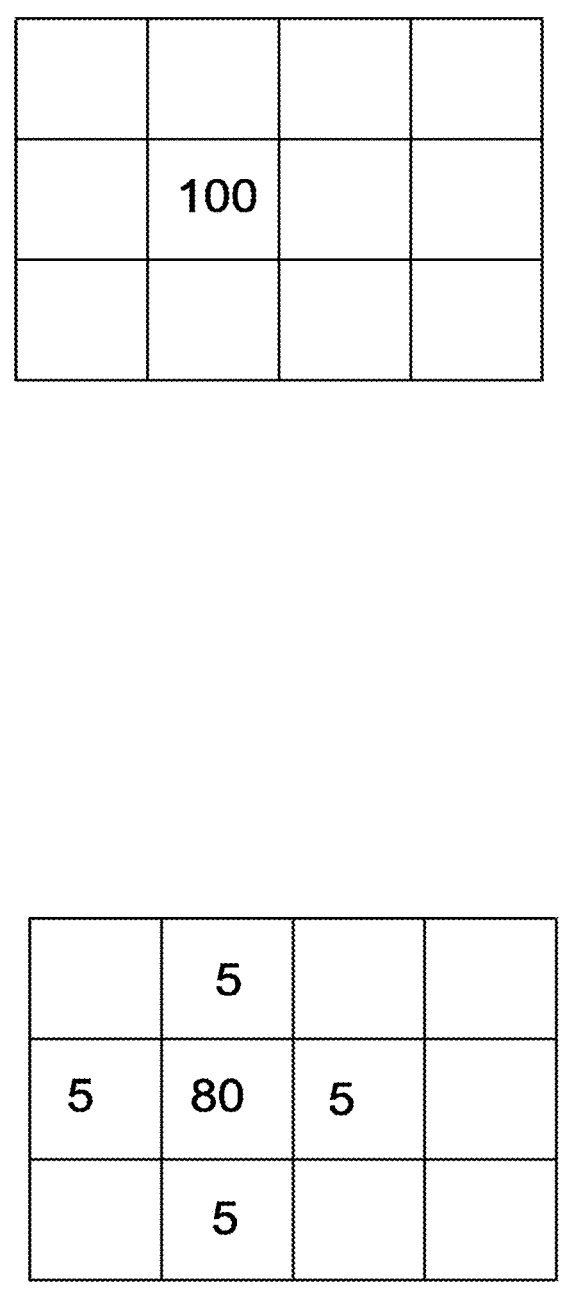

FIG. 7A shows an ideal case of a single-channel detection event in which no cross-talk occurs between the pixels (i.e., crystal elements) in a scintillator crystal array. That is, 100% of the detected energy remains in the pixel that absorbed the gamma ray. FIG. 7B shows a case of 5% cross-talk in a single-channel event. That is, when the light sharing is 5%, then each adjacent pixel receiving 5% of the photons with 80% remaining in the original pixel.

Figures 8A, 8B:
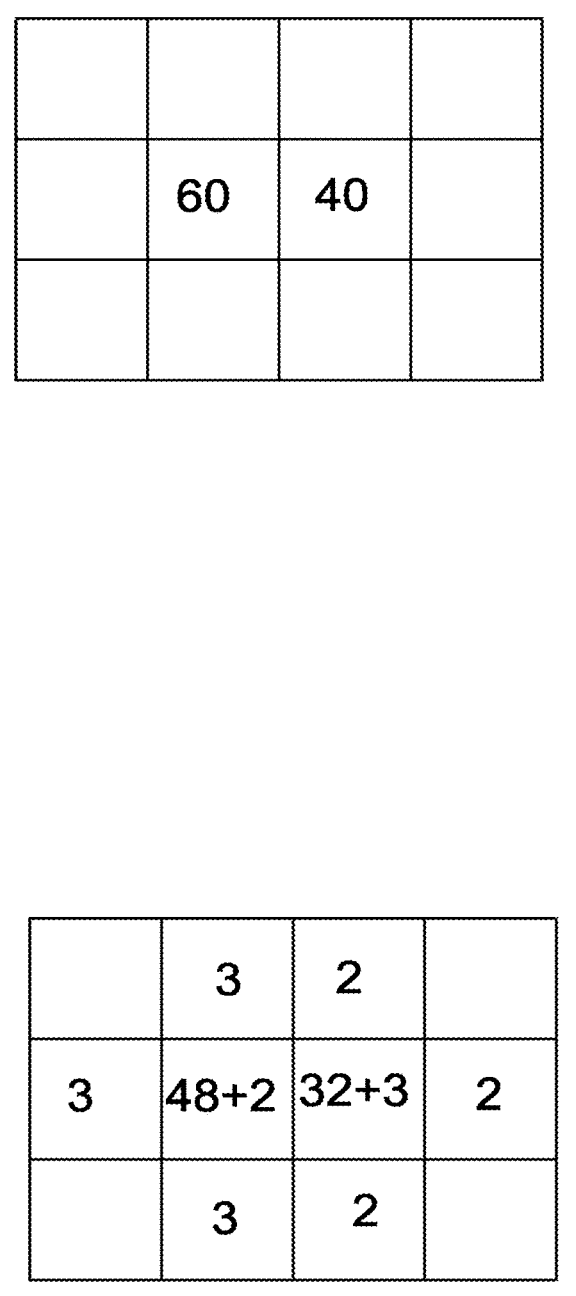

FIGS. 8A and 8B respectively show the ideal case of no cross-talk and 5% cross-talk for a two-hit multi-channel detection event (e.g., one primary gamma ray and one scattered gamma ray). This non-limiting example assumes 5% optical cross-talk between neighbouring crystals, and a 10% TOT threshold. In FIG. 8A, the summed energy is 60+40=100, which is the same as in the single-channel case. In FIG. 8B, however, the summed energy is (48+2)+(32+3)=85, which is 5% greater than in the single-channel case. This difference arises because, in the multi-channel case, 3% and 2% of the total energy are coupled via cross-talk into channels that exceed the threshold, whereas, in the single-channel, all of the channels into which energy is coupled via cross-talk are below the threshold. That is, in the single-channel case none of the cross-talk energy is included in the measured energy (i.e., the energy above the threshold), whereas in the two-channel case 5% of the cross-talk energy is recaptured in the measured energy. Thus, even when the detector elements have a perfectly linear response, cross-talk can result in the measured-and-summed energy from a multi-channel detection deviating from the measured energy of the single-channel detection.

In the case of cross-talk, the summed/measured energy for single-channel and two-channel detection can be given by $$E(f, \delta_1, \delta_2),$$

wherein f is the fraction of energy left in the first crystal (i.e., the crystal absorbing energy from the primary gamma ray), and $\delta_1$ and $\delta_2$ are the optical cross-talk of first and second crystals with their respective neighbouring crystals. In certain implementations, a different optical cross-talk can be used for each adjacent crystal, and the individual detectors are assumed to have a perfectly linear response to energy. For the multi-channel case, $$E(f, \delta_1, \delta_2) = E_0\{f(1-4\delta_1) + f\delta_1 + +(1-f)(1-4\delta_2) + (1-f)\delta_2\}$$

wherein $E_0$ is the energy that would be measured in the absence of cross-talk, the first term on the right-hand side, $E_0 f(1-4\delta_1)$, is the energy in the first crystal minus the losses due to cross-talk, the second term on the right-hand side, $E_0 f \delta_1$, is the energy obtained by the second crystal due to cross-talk from the first crystal, the third term, $E_0(1-f)(1-4\delta_2)$, is the energy in the second crystal minus the losses due to cross-talk, and the fourth term on the right-hand side, $E_0(1-f)\delta_2$ is the energy obtained by the first crystal due to cross-talk from the second crystal. For example, in FIG. 8B, $f=0.6$ and $\delta_1=\delta_2=0.05$, resulting in the first term being $E_0 f(1-4\delta_1)=0.48E_0$, the second term being $E_0 f \delta_1=0.03E_0$, the third term being $E_0(1-f)(1-4\delta_2)=0.32E_0$, the fourth term being $E_0(1-f)\delta_2=0.02E_0$. The above expression for the two-hit multi-channel case, can simplify to $$E(f,\delta_1,\delta_2)=E_0\{f(1-3\delta_1)+(1-f)(1-3\delta_2)\}.$$

For the single-channel case $f=1$, and the energy is given by $$E(1,\delta_1,\delta_2)=E_0(1-4\delta_1).$$

The energy difference can then be given by $$\begin{aligned}\Delta E(f,\delta_1,\delta_2) &= E(f,\delta_1,\delta_2) - E(1,\delta_1,\delta_2) \\ &= E_0(f(1-3\delta_1)+(1-f)(1-3\delta_2)) - E_0(1-4\delta_1) \\ &= E_0(\delta_1+3f(\delta_2-\delta_1))\end{aligned}$$

Similar expressions can be derived for multi-channel events with three hits, four hits, etc.

In certain implementations, when the two channels of multi-channel even are not adjacent (e.g., there is a crystal element between the two channels, as illustrated in FIG. 5), then the cross-talk energy is not couple into a channel that exceeds the threshold, and the summed energy is the same as measured during a single-channel event.

In view of the above discussion, it can be observed that, for a given energy measurement, if the energy of the gamma ray is shared among multiple channels, the summed uncalibrated energy depends on the level of cross-talk. For example, the above expression for $\Delta E(f,\delta_1,\delta_2)$ exhibits an energy shift that is proportional to the level of optical cross-talk $\delta_1$ and $\delta_2$. Further, if the cross-talk varies from crystal to crystal, the shift can also change as a function energy sharing. Accordingly, the amount of energy shift can be parametrized by the spatially-dependent cross-talk parameters $\delta_1(\vec{X})$ and $\delta_2(\vec{X})$, which can be obtained using a lookup table indexed by the position $\vec{X}$. That is, in certain implementations, the energy calibration 185 includes a correction look-up-table in the space of $\vec{x}$, which represents the degree of energy sharing between crystals. For each multi-channel event, the energy calibration 185 can be applied in step 140 by calculating a position $\vec{X}$ for the multi-channel event, using the position $\vec{X}$ to lookup the spatially-dependent cross-talk parameters $\delta_1(\vec{X})$ and $\delta\delta_2(\vec{X})$, and then correcting the summed energy for the multi-channel using a correction factor, such as the correction factor $(\delta_1+3f(\delta_2-\delta_1))$ indicated above for two-hit multi-channel events.

Figure 9:
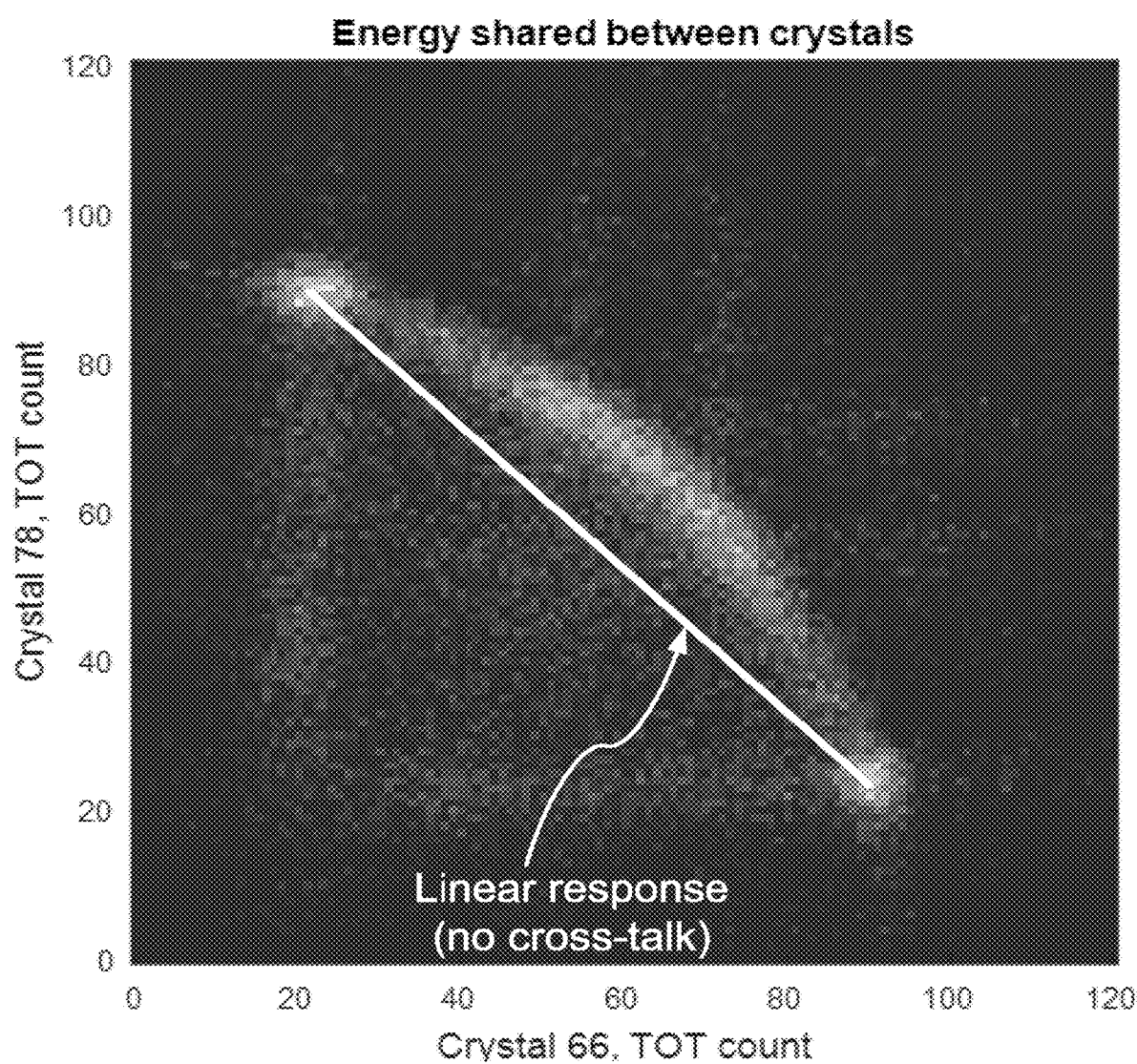
FIG. 9 shows a plot of a count density for multi-channel events as a function of a TOT value measured at a first crystal (Crystal 78) and a TOT value measured at a second crystal (Crystal 66), which are adjacent to each other, according to one implementation.

The nonlinearity due to cross-talk can also be observed in FIG. 9, which uses a grey scale to represent the number of counts measured for multi-channel events between adjacent crystals (i.e., Crystal ID 66 and Crystal ID 78) as a function of the measured energy in the respective crystal elements. For reference, a line corresponding to the linear response that would be observed in the absence of cross-talk has been superimposed on the plot in FIG. 9. FIG. 9 shows that, for non-linear energy measurements, if the energy of the gamma ray is shared by multiple channels, the summed uncalibrated energy depends on how the energy is distributed.

In certain implementations, an initial, rough energy calibration is used to approximately calibrate the non-linearity of the energy measurement in individual channels. For example, the initial energy calibration can correct for the nonlinear relation between the TOT value and the energy. In certain implementations, the initial, rough energy calibration is performed using single-channel events only.

As discussed above, the energy correction can be spatially dependent and based on a lookup table that is indexed using the multi-channel event coordinates $\vec{X}$. Now, a non-limiting method of determining the coordinates $\vec{X}$ is provided. Multi-channel events can be collected from calibration (PET) data that has either been corrected using the initial, rough calibration, which is discussed above, or from measurements using a gamma ray source with known energy. Then, a total energy $E_{sum}=\Sigma_i^n E_i^w$ and an energy weighted 2D coordinate $\vec{X}=\Sigma_i^n \vec{x}_i E_i^w/E_{sum}$ can be calculated for each multi-channel event. As discussed above $\vec{x}_i$ is a central coordinate of channel i, $E_i$ is an energy value (e.g., either a non-linearity calibrated energy value or raw energy value), and w is an energy weight, which can be any value except for 0.

In certain implementations, an energy window can be used to filter out hits that have energies that are either too low or too high to be considered reliable.

Figure 10A:
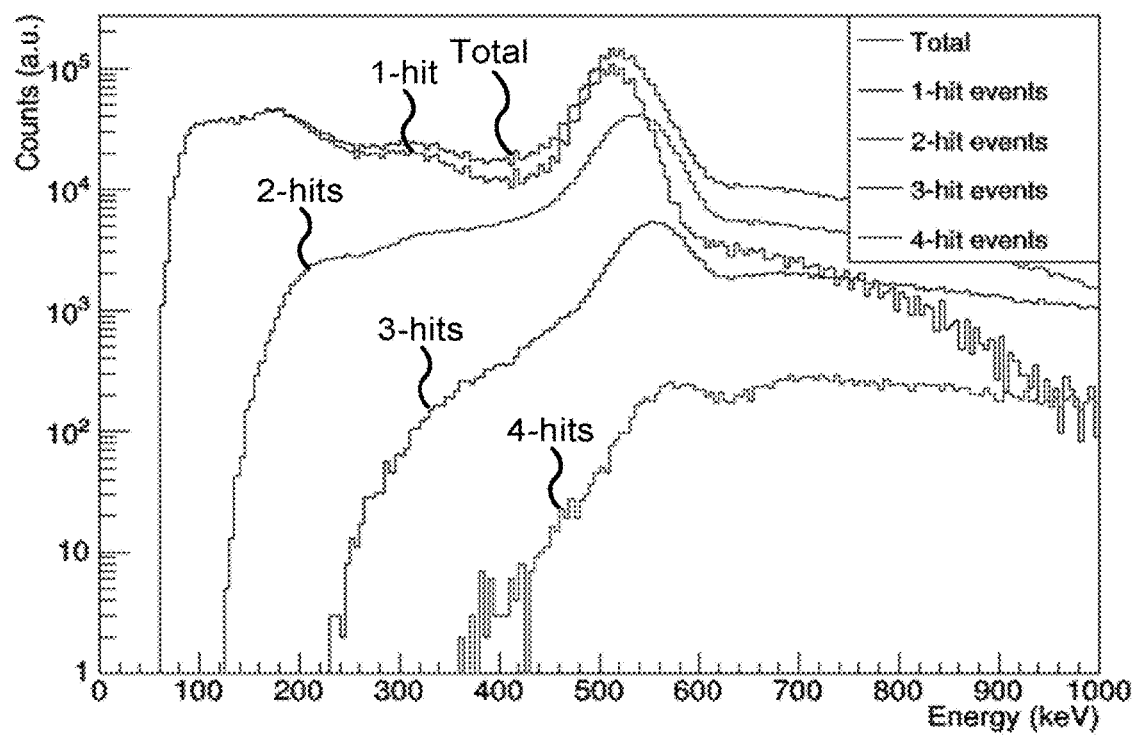
FIG. 10A shows a histogram plot of summed energies without energy corrections for single-channel detection events (1-hit), two-channel detection events (2-hits), three-channel detection events (3-hits), and four-channel detection events (4-hits), according to one implementation.

In certain implementations, the generation of the energy calibration at step 180 can include segmenting the full 2D space of coordinates $\vec{X}$ into blocks. In each block, a histogram can be generated of the number of counts as a function of the total energy, as shown in FIG. 10A. For example, in FIG. 10A, the histogram labeled "1-hit" corresponds to the single-channel events. The histogram labeled "2-hits" corresponds to the multi-channel events with two hits (e.g., the first-order Compton scatter). The histogram labeled "3-hits" corresponds to the multi-channel events with three hits (e.g., the second-order Compton scatter having one primary gamma ray and two scattered gamma rays), and so forth. In FIG. 10A, the peak of the histograms for the multi-channel events do not occur at the known energy of 511 keV for positron emission. Accordingly, the energy of the peak of the histogram can be determined, and the correction parameters can be selected to shift the peak to the known energy (e.g., 511 keV when a positron-emission source is used).

In certain implementations, the correction parameter is either a multiplicative or additive constant. For example, when the correction parameter $C(\vec{X})$ is a multiplicative constant, the correction parameter for a given block can be calculated either as the ratio of the incident gamma energy $E_0$ (e.g., 511 keV) to the central energy (e.g., the peak energy) in the histogram $E_{hist}=\text{mode}(E_{sum}(\vec{X}))$:

$$C(\vec{X})=E_0/E_{hist},$$

wherein the operator mode(·) returns the value in a histogram that occurs most often. Alternatively, instead of using the mode as the central energy that is to be shifted to the known energy, the central/peak energy of the histogram can be provided by the median or the mean histogram, or it can be determined by fitting the histogram to a functional form, such as a Gaussian. Any method can be used for determining the central energy of the histogram $E_{hist}$ (e.g., a geometric or arithmetic mean, etc.) without departing from the spirit of the methods described herein, as would be understood by a person of ordinary skill in the art.

Further, when the correction parameter is an additive constant, rather than a multiplicative constant, the correction parameter $C(\vec{X})$ for a given block can be calculated as the a difference between the incident gamma energy $E_0$ (e.g., 511 keV) and the central/peak histogram energy $E_{hist}$, i.e., $$C(\vec{X})=E_0-E_{hist}$$

In certain implementations, when a given block is determined to lack sufficient counts to perform a reliable statistical analysis, thereby preventing an accurate determination of the peak energy $E_{hist}$, the correction parameter $C(\vec{X})$ will be assigned a default value (e.g., a value of 1 when the correction parameter $C(\vec{X})$ is multiplicative and a value of 0 when the correction parameter $C(\vec{X})$ is additive).

In certain implementations, better energy resolution can be achieved by using different correction look-up-tables and correction parameters $C(\vec{X})$ that depend on the multiplicity (i.e., number of hits). For example, different correction parameters $C(\vec{X})$ can be generated for various levels of multiplicity, e.g., $C_2(\vec{X})$ for two-crystal events (i.e., two hits), $C_3(\vec{X})$ for three-crystal events (i.e., two hits), etc.

Further, the size of the blocks can be different for the different correction parameters $C_2(\vec{X})$, $C_3(\vec{X})$, etc. For example, the respective segmentations (e.g., block size and the degree of coarse graining) of coordinate space $\vec{X}$ corresponding to different multiplicity levels can depend on predefined criteria such as a predefined goal for the resolution and a predefined statistical requirements (e.g., a desired signal-to-noise ratio SNR). For example, the block size at a given multiplicity (i.e., number of hits per multi-channel event) can be based on ensuring that the counts per block exceeds a predefined threshold, resulting in larger block sizes for higher multiplicities. That is, count rates can decrease as the multiplicity increases. Further, multiplicities in which the block size exceeds a predefined maximum resolution limit can be discarded and omitted from the reconstruction.

For example, FIG. 10A shows a low count rate at a multiplicity of 4-hits, making it difficult to determine a peak/central histogram energy for the "4-hits" multiplicity. Accordingly, these counts might be discarded and not used during tomographic image reconstruction. If that is the case, then then maximum multiplicity level would be "3-hits." Accordingly, the maximum multiplicity level and the required statistics of collected data are pre-determined by the goal of resolution.

At step 140, to apply the energy calibration 185 and correct the PET data 105, the summed energy $E_{sum}$ are calculated, from the PET data 105, for each of the multi-channel events of the PET data 105 that were determined in step 120. Further, the coordinates $\vec{X}$ that were calculated in step 130 are used to lookup, in the energy calibration 185, the correction factor, $C_n(\vec{X})$ for each of the multi-channel event, wherein n refers to the multiplicity. Next, the correction parameter/factor $C_n(\vec{X})$ is applied to the summed energy $E_{sum}$. For example, when the correction factor $C(\vec{X})$ is multiplicative, then the corrected energy is given by $$E_{cor}=E_{sum}C(\vec{X}).$$

when the correction factor $C(\vec{X})$ is additive, then the corrected energy is given by $$E_{cor}=E_{sum}+C(\vec{X}).$$

For certain applications, the reconstruction depends only on whether the energy is within the range of an energy window. For example, the energy window can be used to select which coincidence counts are considered reliable enough to use in image reconstruction. In this case, the actual energy value is not significant, and a simpler and computationally faster approach is to shift the energy window, rather than shifting the summed energy values. For example, when the energy window is $[E_{min}, E_{max}]$ and the correction factor $C(\vec{X})$ is multiplicative, the shifted energy window can be given by $[E_{Min}/C_n(\vec{X}), E_{Max}/C_n(\vec{X})]$. Similarly, when the correction factor $C(\vec{X})$ is additive, the shifted energy window can be given by $[E_{Min}-C_n(\vec{X}), E_{Max}-C_n(\vec{X})]$. Thus, for each multiplicity and block, the correction factor $C(\vec{X})$ can be applied once to each end of the energy window $E_{Min}$ and $E_{Max}$, rather than being repeatedly applied to each of the summed energies $E_{sum}$ within a given block.

Figure 10B:
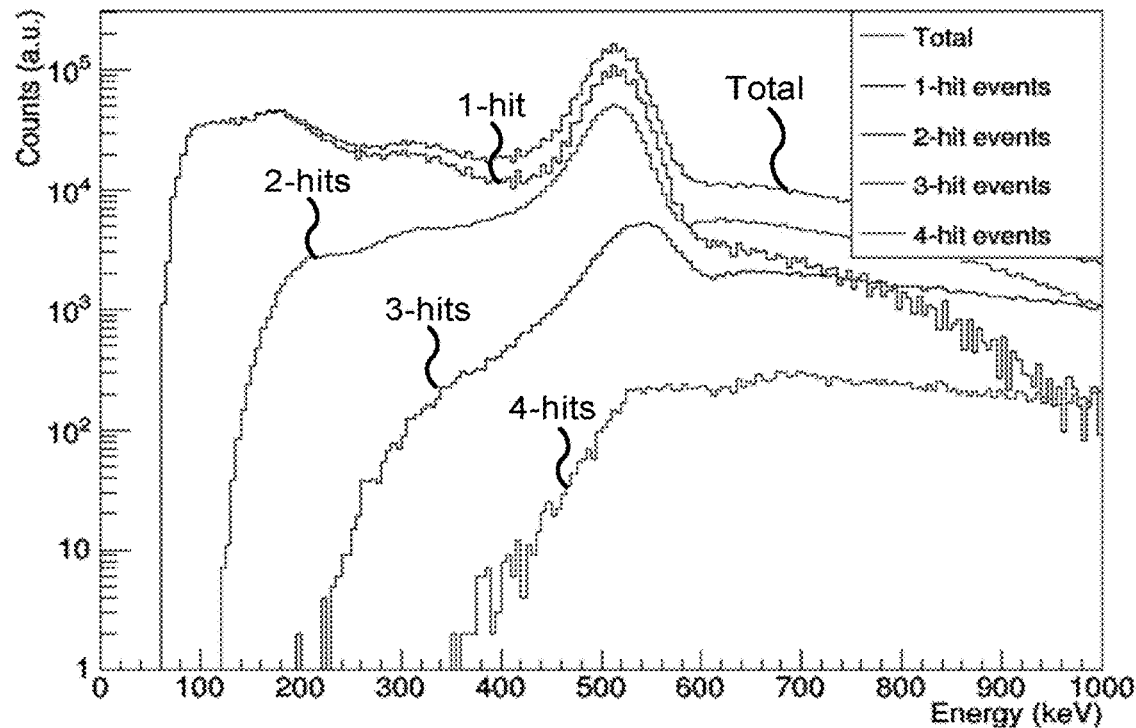
FIG. 10B shows a histogram plot of summed energies with energy corrections for the single-channel detection events (1-hit), the two-channel detection events (2-hits), the three-channel detection events (3-hits), and the four-channel detection events (4-hits), according to one implementation.

FIG. 10B shows histograms similar to those in FIG. 10A, except in FIG. 10B the corrected PET data is used. As can be seen, the energy peak for the 2-hits multi-channel events has been shifted to agree much more closely with the known energy (i.e., 511 keV). Similarly, the energy peak for the 3-hits multi-channel events has been shifted towards the known energy.

In view of the above, the energy calibration methods described herein have several advantages. First, accurate energy measurements can be recovered using these methods, and the measured energies for multi-channel/crystal events become comparable to the single-channel/crystal events. Second, residual non-linearities remaining after the initial, rough energy calibrations of TOT measurements can be mitigated. Third, the methods described herein can be computationally efficient and can be easily implemented using lookup tables. Fourth, the methods described herein can be robust against unphysical results (e.g., the corrected energies will not produce negative energy values).

The various implementations of the methods described herein can include correcting the shift of the total/summed energy arising in multi-channel events due to any non-linear energy measurement and/or cross-talk between channels of a pixelated gamma detector. These methods can include (i) obtaining calibration data using a gamma-ray source with known energy for the gamma rays; (ii) calculating energy-weighted position of the multi-channel events; (iii) generating correction look-up-tables by comparing summed energies with known energy of the gamma rays; (iv) and applying the correction factors in the look-up-tables to multi-channel events in PET data from a PET scan.

In certain implementations, the gamma detector can include a scintillator crystal that is segmented into an array of separate crystal elements, or, alternatively, in certain other implementations, the gamma detector can include a scintillator crystal that is not segmented into an array of separate crystal elements. Further, in certain other implementations, the crystal elements can be one-on-one coupled to the photodetectors, and, in certain other implementations, the crystal elements might not be one-on-one coupled to the photodetectors.

In certain implementations, an option is provided to apply an initial, rough non-linear correction to individual energy readings, thereby improving performance of the energy calibration. In certain implementations, this initial, rough non-linear correction can be performed using look-up-tables or parameterized formulas. The parameterized formulas could be based on first principles or can be empirically/experimentally determined.

In certain implementations, multi-channel events are recognized and selected/filtered based one multiple channels all reporting non-zero energies within a pre-defined time window, and the channels/crystals reporting non-zero energies within the pre-defined time window being within a pre-defined distance.

In certain implementations, for each multi-channel event, either the non-linear corrected or raw energy readings are used to calculate an energy weighted 2D coordinate. The energies are weighted by pre-defined non-zero power w.

In certain implementations, the multi-channel events from the calibration data are grouped/clustered into block according to their 2D coordinates and their multiplicity (i.e., the number of hits/channels in the multi-channel event). In each group, the central/peak energy of a histogram is determined, and the correction factor (e.g., either multiplicative or additive) is calculated to shift the central/peak energy to the known energy of the gamma-ray source. If there is not enough counts to determine the central/peak energy of the histogram peak, the correction factor is set to a default value (e.g., the correction factor is set to 1 for a multiplicative correction factor or the correction factor is set to 0 for an additive correction factor).

In certain implementations, the segmentation into blocks in the two-dimensional (2D) coordinates of the pixelated gamma detector is performed to generate block sizes at the respective multiplicities based on specified goals/criteria for the resolution and/or the number of counts per block that are required to achieve a reliable estimate of the energy shift to be corrected. For example, the block size can be selected to affect a trade-off between balancing the improvement in energy resolution and resources needed for calibration.

In certain implementations, for each level of multiplicity, the tabulation of the correction factors can form a correction look-up-table (LUT) in the space of the energy weighted 2D coordinate.

In certain implementations, depending on the segmentation in multiplicity, there could either be one LUT or multiple LUTs. When there are multiple LUTs generated, the block size used in the segmentation of the 2D coordinates in different LUTs does not need to be the same. Rather, the block size used in the segmentation of different multiplicities to generate different LUTs can be determined by the count density, the accuracy of the energy correction, and/or the magnitude of the energy correction. The LUTs can be used for off-line correction or for on-line correction during data acquisition (e.g., in real time).

In certain implementations, once all LUTs are calibrated, the total energies of multi-channel events by searching for correction factors in LUTs using an event's energy weighted coordinate and number of hits.

In certain implementations, for applications with a goal of selecting events within certain energy range/window, the total energy correction can be directly applied to energy windows used for event selection. And the corrected energy window will then be applied to uncorrected data to decide whether or not to keep the event and use the event for image reconstruction. In this case, the corrected PET data is the PET data absent events/counts outside of the shifted energy window, without a shift being applied to the recorded energy values of the events.

Although the non-limiting examples discussed above illustrate the methods described herein using PET data and a PET system, the methods described herein can be applied to other imaging systems including, e.g., a single-photon emission CT system (SPECT), as would be understood by a person of ordinary skill in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An imaging apparatus, comprising:
processing circuitry configured to
obtain emission data representing positions and energies of gamma rays incident at a plurality of detector elements, detector elements of the plurality of detector elements leaking a part of a gamma-ray detection signal to adjacent detector elements of the plurality of detector elements,
obtain an energy calibration including one or more correction factors that correct for an energy shift occurring during multi-channel detection in which a primary gamma ray is scattered and an energy of a scattered gamma ray is absorbed in a different detector element of the plurality of detector elements than a detector element absorbing a part of an energy of the primary gamma ray,
determine which detection events of the emission data correspond to the multi-channel detection to select multi-channel events, and
apply the one or more correction factors to respective energies of the selected multi-channel events to generate corrected emission data, wherein
the energy shift is due to cross-talk produced in the multi-channel detection,
the energy shift is a loss of energy level of the gamma rays,
the energy calibration includes the one or more correction factors for respective one or more numbers of hits of gamma rays at the plurality of detector elements, and
the processing circuitry is configured to select the multi-channel events by grouping the multi-channel events in terms of the one or more numbers of hits, and to apply the one or more correction factors to the respective energies of the selected multi-channel events having the corresponding one or more numbers of hits.

2. The apparatus according to claim 1, wherein the processing circuitry is further configured to apply the one or more correction factors to the respective energies of the selected multi-channel events by, for each multi-channel event of the selected multi-channel events,
summing energies of detection events of the multi-channel event to generate a summed energy, which is the respective energy of the multi-channel event, and
summing the summed energy and an energy correction that is based on the one or more correction factors to generated a corrected energy of the multi-channel event.

3. The apparatus according to claim 1, wherein the processing circuitry is further configured to apply the correction factor to the respective energies of the selected multi-channel events by, for each multi-channel event of the selected multi-channel events,
    summing energies of detection events of the multi-channel event to generate a summed energy, which is the respective energy of the multi-channel event, and
    multiplying the summed energy and an energy correction ratio that is based on the one or more correction factors to generated a corrected energy of the multi-channel event.

4. The apparatus according to claim 1, wherein the processing circuitry is further configured to apply the one or more correction factors to the respective energies of the selected multi-channel events by
    shifting an energy window by subtracting one of the one or more correction factors from a maximum energy of the energy window and subtracting one of the one or more correction factors from a minimum energy of the energy window, the energy window being a range of energies from the minimum energy to the maximum energy,
    summing, for each multi-channel event of the selected multi-channel events, energies of detection events of the multi-channel event to generate a summed energy, which is the respective energy of the multi-channel event, and
    selecting multi-channel events having summed energies within the shifted energy range to be included in the corrected emission data.

5. The apparatus according to claim 1, wherein the processing circuitry is further configured to apply the one or more correction factors to the respective energies of the selected multi-channel events by
    shifting an energy window by dividing a maximum energy of the energy window by one of the one or more correction factors and dividing a minimum energy of the energy window by one of the one or more correction factors, the energy window being a range of energies from the minimum energy to the maximum energy,
    summing, for each multi-channel event of the selected multi-channel events, energies of detection events of the multi-channel event to generate a summed energy, which is the respective energy of the multi-channel event, and
    selecting multi-channel events having summed energies within the shifted energy range to be included in the corrected emission data.

6. The apparatus according to claim 1, wherein the processing circuitry is further configured to
    obtain the emission data, wherein the emission data represents times of when the gamma rays are detected in addition to representing the positions and the energies of the detected gamma rays, and the emission data are restricted to include only detection events exceeding a minimum energy threshold, and
    determine which of the detection events correspond to the multi-channel detection by selecting two or more detection events as corresponding to a same multi-channel events based on one or more of a proximity of positions of the two or more detection events, a proximity of times of the two or more detection events, and proximity of a predefined energy to a sum of energies of the two or more detection events.

7. The apparatus according to claim 1, wherein the processing circuitry is further configured to
    determine which of the detection events correspond to the multi-channel detection by grouping the selected multi-channel events according to respective multiplicities, including a first multiplicity of two-hit events including first-order scatter and a second multiplicity of three-hit events including second-order scatter,
    obtain the energy calibration including the one or more correction factors and another one or more correction factors, wherein the one or more correction factors corresponds to the first multiplicity and the another one or more correction factors corresponds to the second multiplicity, and
    apply the one or more correction factors to the respective energies of the selected multi-channel events by using the one or more correction factors to correct the selected multi-channel events grouped into the first multiplicity and using the another one or more correction factors to correct the selected multi-channel events grouped into the second multiplicity.

8. The apparatus according to claim 1, wherein the processing circuitry is further configured to
    obtain the energy calibration, wherein the energy calibration includes a plurality of correction factors that are indexed according to spatial coordinates that correspond to the plurality of detector elements, wherein the a plurality of correction factors includes the one or more correction factors, and
    apply the plurality of correction factors to respective energies of the selected multi-channel events by selecting, for a multi-channel event of the selected multi-channel events, a correction factor of the plurality of correction factors corresponding to a weighted average of positions of the detection events of the multi-channel event.

9. The apparatus according to claim 8, wherein the processing circuitry is further configured to obtain the energy calibration, wherein the weighted average of the positions of the detection events of the multi-channel even is calculated using a normalized weighted sum of the positions of the detection events in which the weights are respective energies of the detection events raised a power w, which is a non-zero real number.

10. The apparatus according to claim 8, wherein the processing circuitry is further configured to obtain the energy calibration, wherein the plurality of correction factors are indexed according to the spatial coordinates, the spatial coordinates are segmented into blocks each of which corresponds to a respective correction factor of the plurality of correction factors, a size of the blocks being selected to satisfy one or more of a predefined spatial-resolution criterion and a predefined count criterion regarding an accuracy or reliability of the plurality of correction factors.

11. The apparatus according to claim 8, wherein the processing circuitry is further configured to obtain the energy calibration, wherein the size of the blocks is different for corrections factor of the plurality of correction factors corresponding to different multiplicities of multi-channel events.

12. The apparatus according to claim 1, wherein the processing circuitry is further configured to perform an initial nonlinear-energy correction to the emission data prior to applying the one or more correction factors to respective energies of the selected multi-channel events.

13. The apparatus according to claim 12, wherein the processing circuitry is further configured to perform the initial nonlinear-energy correction, wherein the nonlinear energy correction corrects for a nonlinear relation between a measured value and an actual energy of a detected gamma ray.

14. The apparatus according to claim 1, wherein the processing circuitry is further configured to generate the energy calibration by
 obtaining calibration data,
 determining which detection events of the calibration data correspond to the multi-channel detection to select multi-channel calibration events,
 summing, for each multi-channel calibration event of the selected multi-channel calibration events, energies of detection events of the multi-channel event to generate a summed energy, which is the respective energy of the multi-channel calibration event,
 estimating a representative summed energy of the selected multi-channel calibration events by performing an analysis on the summed energies, and
 setting the one or more correction factors to shift the representative summed energy to a predefined energy.

15. The apparatus according to claim 14, wherein the processing circuitry is further configured to set the one or more correction factors to include a multiplicative correction factor or an additive correction factor.

16. The apparatus according to claim 14, wherein the processing circuitry is further configured to estimate the representative summed energy by
 determining, for segmented multi-channel calibration events within a coordinate block of plurality of detectors, a distribution of a number of multi-channel calibration events as a function of the summed energies, and
 estimating the representative summed energy as one of a median of the distribution, a mode of the distribution, and a mean of the distribution.

17. The apparatus according to claim 1, wherein
 the apparatus is one of a positron emission tomography (PET) system and a single-photon emission computed tomography (SPECT) system, and
 the processing circuitry is further configured to reconstruct an image using the corrected emission data.

18. The apparatus according to claim 1, wherein the energy shift is proportional to optical cross-talk.

19. An imaging method, comprising:
 obtaining emission data representing positions and energies of gamma rays incident at a plurality of detector elements, detector elements of the plurality of detector elements leaking a part of a gamma-ray detection signal to adjacent detector elements of the plurality of detector elements,
 obtaining an energy calibration including one or more correction factors that correct for an energy shift occurring during multi-channel detection in which a primary gamma ray is scattered and an energy of a scattered gamma ray is absorbed in a different detector element of the plurality of detector elements than a detector element absorbing a part of an energy of the primary gamma ray,
 determining which detection events of the emission data correspond to the multi-channel detection to select multi-channel events, and
 applying the one or more correction factors to respective energies of the selected multi-channel events to generate corrected emission data, wherein
 the energy shift is due to cross-talk produced in the multi-channel detection,
 the energy shift is a loss of energy level of the gamma rays,
 the energy calibration includes the one or more correction factors for respective one or more numbers of hits of gamma rays at the plurality of detector elements, and
 the method further includes selecting the multi-channel events by grouping the multi-channel events in terms of the one or more numbers of hits, and to apply the one or more correction factors to the respective energies of the selected multi-channel events having the corresponding one or more numbers of hits.

20. The method according to claim 19, wherein the correcting of the calibration data further includes generating the energy calibration by
 obtaining calibration data,
 determining which detection events of the calibration data correspond to the multi-channel detection to select multi-channel calibration events,
 summing, for each multi-channel calibration event of the selected multi-channel calibration events, energies of detection events of the multi-channel event to generate a summed energy, which is the respective energy of the multi-channel calibration event,
 estimating a representative summed energy of the selected multi-channel calibration events by performing an analysis on the summed energies, and
 setting the one or more correction factors to shift the representative summed energy to a predefined energy.

21. A non-transitory computer readable storage medium including executable instructions, wherein the instructions, when executed by circuitry, cause the circuitry to perform the method according to claim 19.

* * * * *